(12) United States Patent
Krauss et al.

(10) Patent No.: US 7,759,389 B2
(45) Date of Patent: Jul. 20, 2010

(54) CHROMAN DERIVATIVES AND USES THEREOF

(75) Inventors: Nancy Elisabeth Krauss, Mountain View, CA (US); Shu-Hai Zhao, Cupertino, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 1216 days.

(21) Appl. No.: 11/315,392

(22) Filed: Dec. 21, 2005

(65) Prior Publication Data

US 2006/0148888 A1 Jul. 6, 2006

Related U.S. Application Data

(60) Provisional application No. 60/637,854, filed on Dec. 21, 2004.

(51) Int. Cl.
 *A61K 31/353* (2006.01)
 *A61K 31/4025* (2006.01)
 *C07D 311/04* (2006.01)
 *C07D 405/06* (2006.01)

(52) U.S. Cl. .................. 514/422; 514/456; 549/355; 549/407; 549/467; 548/525

(58) Field of Classification Search .............. 549/407, 549/355, 467; 514/456, 422; 548/525
See application file for complete search history.

(56) References Cited

U.S. PATENT DOCUMENTS

| | | | |
|---|---|---|---|
| 5,137,901 A | 8/1992 | Junge et al. |
| 5,374,643 A | 12/1994 | Atwal et al. |
| 5,412,117 A | 5/1995 | Koga et al. |
| 5,614,633 A | 3/1997 | Koga et al. |
| 5,627,138 A | 5/1997 | Anderson et al. |
| 5,637,624 A | 6/1997 | Schaus et al. |
| 5,646,308 A | 7/1997 | Koga et al. |
| 5,663,194 A | 9/1997 | Mewshaw |
| 5,719,182 A | 2/1998 | Cousins et al. |
| 5,739,135 A | 4/1998 | Biller et al. |
| 5,869,478 A | 2/1999 | Ding et al. |
| 5,874,446 A | 2/1999 | Koga et al. |
| 5,883,099 A | 3/1999 | Biller et al. |
| 5,935,958 A | 8/1999 | Kozlowski et al. |
| 5,977,167 A | 11/1999 | Koga et al. |
| 6,083,982 A | 7/2000 | Wechter et al. |
| 6,150,402 A | 11/2000 | Wechter et al. |
| 6,214,881 B1 | 4/2001 | Xiang |
| 6,448,243 B1 | 9/2002 | Kitazawa et al. |
| 6,479,536 B1 | 11/2002 | Ohkawa et al. |
| 6,559,144 B2 | 5/2003 | Diefenbach et al. |
| 6,605,632 B1 | 8/2003 | Lesieur et al. |
| 6,613,805 B2 | 9/2003 | Kato et al. |
| 6,638,972 B2 | 10/2003 | Kelly et al. |
| 6,660,752 B2 | 12/2003 | O'Connor et al. |
| 6,706,757 B2 | 3/2004 | Greenblatt et al. |
| 6,784,314 B2 | 8/2004 | Yamashita et al. |
| 2002/0002177 A1 | 1/2002 | Cousins et al. |
| 2003/0060498 A1 | 3/2003 | Fu |
| 2003/0158175 A1 | 8/2003 | Greenblatt et al. |
| 2004/0024210 A1 | 2/2004 | Johansson et al. |
| 2005/0154053 A1 | 7/2005 | Rhijn et al. |

FOREIGN PATENT DOCUMENTS

| | | |
|---|---|---|
| EP | 0 488 616 A1 | 6/1992 |
| EP | 0 587 180 A2 | 9/1992 |
| EP | 0 747 374 B1 | 12/2001 |
| WO | WO 97/02259 A1 | 1/1997 |
| WO | WO 98/07418 A1 | 2/1998 |
| WO | WO 2005/040355 A2 | 5/2005 |

*Primary Examiner*—Bernard Dentz
(74) *Attorney, Agent, or Firm*—Robert C. Hall

(57) ABSTRACT

Compounds of the formula I:

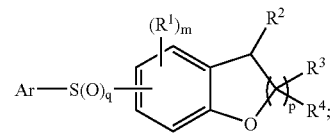

or pharmaceutically acceptable salts thereof,
wherein m, p, q, Ar, $R^1$, $R^2$, $R^3$ and $R^4$ are as defined herein. Also provided are methods for preparing, compositions comprising, and methods for using compounds of formula I.

23 Claims, No Drawings

CHROMAN DERIVATIVES AND USES THEREOF

CROSS REFERENCE TO RELATED APPLICATIONS

This application claims the benefit of priority of U.S. Provisional Patent Application Ser. No. 60/637,854 filed Dec. 21, 2004, the disclosure of which is incorporated herein by reference in its entirety.

FIELD OF THE INVENTION

This invention relates to substituted chroman compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Mol. Pharmacol., 1993, 43, 320-327, A. J. Sleight et al., Neurotransmission, 1995, 11, 1-5, and A. J. Sleight et al., Serotonin ID Research Alert, 1997, 2(3), 115-8.

While some 5-HT6 and 5-HT2A modulators have been disclosed, there continues to be a need for compounds that are useful for modulating the 5-HT6 receptor, the 5-HT2A receptor, or both.

SUMMARY

The invention provides compounds of the formula I:

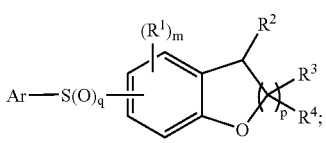

or a pharmaceutically acceptable salt thereof,
wherein:
m is from 0 to 3;
p is from 1 to 3;
q is 0, 1 or 2;
Ar is optionally substituted aryl or optionally substituted heteroaryl;
each $R^1$ is independently halo, alkyl, haloalkyl, heteroalkyl, cyano, —S(O)$_t$—$R^a$, —C(=O)—N$R^b R^c$, —SO$_2$—N$R^b R^c$, —N($R^d$)—C(=O)$R^e$, —C(=O)N($R^d$)—, or —C(=O)—$R^e$, where t is from 0 to 2, and $R^a$, $R^b$, $R^c$, $R^d$ and $R^e$ each independently is hydrogen or alkyl, and;
$R^2$ is

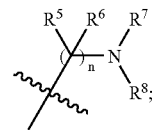

n is from 1 to 3;
$R^3$ and $R^4$ each independently is hydrogen or alkyl;
$R^5$ and $R^6$ each independently is hydrogen or alkyl, or $R^5$ and $R^6$ together may form =N$R^f$ wherein $R^f$ is hydrogen or alkyl; and
$R^7$ and $R^8$ each independently is hydrogen or alkyl, or one of $R^7$ and $R^8$ is hydrogen and the other is an optionally substituted 5- or six membered heteroaryl or heterocyclyl ring containing one or two nitrogens, or $R^7$ and $R^8$ together with the nitrogen to which they are attached may form an amidinyl group, a urea group, a guanidinyl group, or a five- or six-membered heterocyclic ring that optionally includes an additional heteroatom selected from O, N and S and which is optionally substituted with amino, or one of $R^7$ and $R^8$ and one of $R^5$ and $R^6$ together with the atoms to which they are attached may form a five- or six-membered heterocyclic ring that optionally includes an additional heteroatom selected from O, N and S.

The invention also provides methods for preparing, methods of using, and pharmaceutical compositions comprising the aforementioned compounds. One such method is for producing a compound of formula c;

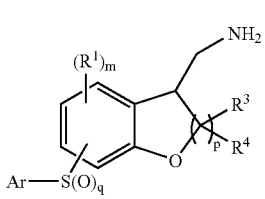

wherein m, p, q, Ar, $R^1$, $R^3$ and $R^4$ are as recited in claim 1, the method comprising reducing a compound of formula b

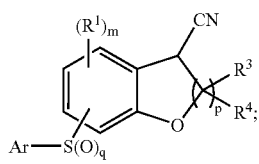

to form the compound of formula c.

DETAILED DESCRIPTION OF THE INVENTION

The invention provides chroman compounds, associated compositions, methods for use as therapeutic agents, and methods of preparation thereof.

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms (i.e., "$C_1$-$C_6$alkyl"). Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH=CH—), 2,2-dimethylethenylene, propenylene, 2-methylpropenylene, butenylene, pentenylene, and the like.

"Alkoxy" means a group —OR, wherein R is alkyl as defined herein. Examples of alkoxy moieties include, but are not limited to, methoxy, ethoxy, isopropoxy, and the like.

"Amidinyl" means a group of the formula:

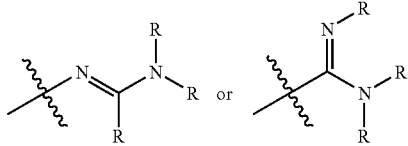

wherein each R independently is hydrogen or alkyl as defined herein.

"Amidinylalkyl" means a group —R—R' wherein R' is amidinyl as defined herein and R is alkylene.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylene" means a divalent aryl radical wherein aryl is as defined herein. "Arylene" includes, for example, ortho-, meta- and para-phenylene (1,2-phenylene, 1,3-phenylene and 1,4-phenylene respectively), which may be optionally substituted as defined herein.

"Arylalkyl" and "Aralkyl", which may be used interchangeably, mean a radical —R—R' where R is an alkylene group and R' is an aryl group as defined herein; e.g., benzyl, phenylethyl, 3-(3-chlorophenyl)-2-methylpentyl, and the like are examples of arylalkyl.

"Cycloalkyl" means a saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R—R', where R is alkylene and R' is cycloalkyl as defined herein.

"Guanidinyl" means a group of the formula

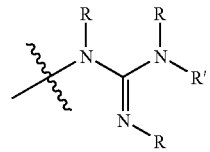

wherein each R independently is hydrogen or alkyl, and R' is hydrogen, alkyl, or phenyl. The phenyl moiety of "guanidinyl" may be optionally substituted as defined herein.

"Guanidinylalkyl" is a group —R—R' wherein R' is guanidinyl as defined herein and R is alkylene.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, methoxy, ethoxy, 2-hydroxyethyl, 3-hydroxypropyl, 2-methoxyethyl, 3-methoxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic monovalent radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyridinyl, pyridazyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof. The aforementioned heteroaryl moieties may be partially saturated. Thus, "heteroaryl" includes "imidazolinyl", tetrahydropyrimidinyl" and the like.

"Heteroarylene" means a divalent heteroaryl radical wherein heteroaryl is as defined herein. "Heteroarylene" may be optionally substituted as defined herein. "Heteroarylene" includes, for example, indolylene, pyrimidinylene, and the like.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, piperidinyl, piperazinyl, homopiperazinyl, azepinyl, pyrrolidinyl, pyrazolidinyl, imidazolinyl, imidazolidinyl, pyridinyl, pyridazinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Imidazolinyl" means a group of the formula

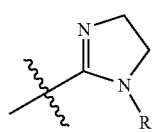

wherein R is hydrogen or alkyl. "Imidazolinyl" may be interchangeably used with "4,5-dihydro-1H-imidazol-2-yl".

"Imidazolinylalkyl" means a group —R—R' wherein R' is imidazolinyl as defind herein and R is alkylene.

"Imidazolinylaminoalkyl" means a group —R—R'—R" wherein R" is imidazolinyl as defined herein, R' is amino, and R is alkylene. The amino moiety of "imidazolinylaminoalkyl" may be optionally substituted with alkyl.

"Pyrimidinylaminoalkyl" means a group —R—R'—R" wherein R" is pyrimidinyl (preferably pyrimidin-2-yl), R' is amino, and R is alkylene. The pyrimidinyl moiety of "pyrimidinylaminoalkyl" may be optionally substituted as defined herein, and the amino moiety of "pyrimidinylaminoalkyl" may be optionally substituted with alkyl.

"Tetrahydropyrimidinyl" means 1,4,5,6-tetrahydropyrimidinyl, preferably 1,4,5,6-tetrahydropyrimidin-2-yl, and may be optionally substituted as defined herein. "Tetrahydropyrimidinyl" includes 5,5-dimethyl-1,4,5,6-tetrahydropyrimidin-2-yl.

"Tetrahydropyrimidinylaminoalkyl" means a group —R—R'—R" wherein R" is tetrahydropyrimidinyl, R' is amino, and R is alkylene. The amino moiety of "tetrahydropyrimidinylaminoalkyl" may be optionally substituted with alkyl.

"Urea" means a group of the formula:

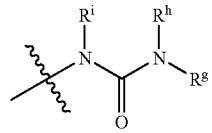

wherein R$^g$, R$^h$ and R$^i$ each independently is hydrogen or alkyl.

"Urealkyl" means a group R—R' wherein R' is urea and R is alkylene.

"Optionally substituted", when used in association with "aryl", phenyl", "heteroaryl", cycloalkyl or "heterocyclyl", means an aryl, phenyl, heteroaryl, or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, monoalkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p 1-92, Elesevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "aminoprotecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Those skilled in the art know how to choose a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature.

Chemical structures shown herein were prepared using ISIS® version 2.2. Any open valency appearing on a carbon, oxygen or nitrogen atom in the structures herein indicates the presence of a hydrogen.

Compounds of the Invention

The invention provides compounds of the formula I:

It should be understood that the scope of this invention encompasses not only the various isomers which may exist but also the various mixture of isomers which may be formed. Furthermore, the scope of the present invention also encompasses solvates and salts of compounds of formula I:

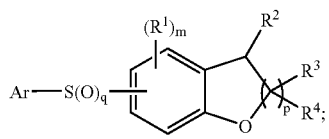

or a pharmaceutically acceptable salt thereof, wherein:

m is from 0 to 3;

p is from 1 to 3;

q is 0, 1 or 2;

Ar is optionally substituted aryl or optionally substituted heteroaryl;

each $R^1$ is independently halo, alkyl, haloalkyl, heteroalkyl, cyano, —S(O)$_t$—$R^a$, —C(=O)—NR$^b$R$^c$, —SO$_2$—NR$^b$R$^c$, —N(R$^d$)—C(=O)—R$^e$, —C(=O)N(R$^d$)—, or —C(=O)—R$^e$, where t is from 0 to 2, and $R^a$, $R^b$, $R^c$, $R^d$ and $R^e$ each independently is hydrogen or alkyl, and;

$R^2$ is

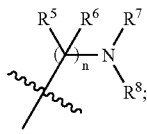

n is from 1 to 3;

$R^3$ and $R^4$ each independently is hydrogen or alkyl;

$R^5$ and $R^6$ each independently is hydrogen or alkyl, or $R^5$ and $R^6$ together may form =NR$^f$ wherein R$^f$ is hydrogen or alkyl; and $R^7$ and $R^8$ each independently is hydrogen or alkyl, or one of $R^7$ and $R^8$ is hydrogen and the other is an optionally substituted 5- or six membered heteroaryl or heterocyclyl containing one or two nitrogens, or $R^7$ and $R^8$ together with the nitrogen to which they are attached may form an amidinyl group, a urea group, a guanidinyl group, or a five- or six-membered heterocyclic ring that optionally includes an additional heteroatom selected from O, N and S and which is optionally substituted with amino, or one of $R^7$ and $R^8$ and one of $R^5$ and $R^6$ together with the atoms to which they are attached may form a five- or six-membered heterocyclic ring that optionally includes an additional heteroatom selected from O, N and S.

In certain embodiments of formula I, p is 1 or 2, and in specific embodiments p is 2. In many embodiments q is 2.

In many embodiments of formula I, $R^3$ and $R^4$ are hydrogen.

In certain embodiments, the compounds of the invention may be of formula II:

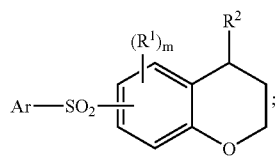

wherein m, Ar, $R^1$ and $R^2$ are as defined herein.

In some embodiments of formula I or formula II, m is 0 or 1, with $R^1$ preferably being halo. In certain embodiments Ar is optionally substuted aryl such as phenyl or naphthyl, each optionally substituted. In other embodiments Ar may be optionally substituted heteroaryl such as thienyl, pyridyl or pyrimidyl, each optionally substituted.

In certain embodiments of the invention, the compounds of formula I or formula II have n equal to 1. In such embodiments $R^7$ and $R^8$ may both be hydrogen. Alternatively one of $R^7$ and $R^8$ may be hydrogen while the other is alkyl, preferably methyl.

In many embodiments of formula I or formula II wherein n is 1, $R^5$ and $R^6$ may be hydrogen.

In other embodiments of formula I or formula II wherein n is 1, one of $R^7$ and $R^8$ is hydrogen and the other may be optionally substituted heteroaryl such as optionally substituted imidazolinyl, optionally substituted pyrimidinyl, optionally substituted pyrrolyl, optionally substituted imidazolyl, or optionally substituted tetrahydropyrimidinyl.

In still other embodiments of formula I or formula II wherein n is 1, $R^7$ and $R^8$ together with the nitrogen to which they are attached may form an amidinyl group.

In yet other embodiments $R^7$ and $R^8$ together with the nitrogen to which they are attached may form a guanidinyl group.

In still other embodiments, $R^7$ and $R^8$ together with the nitrogen to which they are attached may form a urea group.

In further embodiments of formula I or formula II wherein n is 1, $R^5$ and $R^6$ together with the nitrogen to which they are attached may form =$NR^f$ wherein $R^f$ is hydrogen, and wherein $R^5$ and $R^6$ are hydrogen.

In still further embodiments of formula I or formula II wherein n is 1, one of $R^7$ and $R^8$ and one of $R^5$ and $R^6$ together with the atoms to which they are attached may form an imidazolinyl ring.

In still other embodiments of formula I or formula II wherein n is 1, one of $R^7$ and $R^8$ is hydrogen and the other is pyrrolidinyl.

In certain embodiments of the invention, the compounds of formula I or formula II have n equal to 2. In such embodiments $R^7$ and $R^8$ may both be hydrogen, or aternatively one of $R^5$ and $R^6$ may be hydrogen while the other is alkyl, preferably methyl.

In many embodiments of formula I or formula II wherein n is 2, $R^5$ and $R^6$ may be hydrogen.

In other embodiments of formula I or formula II wherein n is 2, one of $R^7$ and $R^8$ is hydrogen and the other may be optionally substituted heteroaryl such as optionally substituted imidazolinyl, optionally substituted pyrimidinyl, optionally substituted pyrrolyl, optionally substituted imidazolyl, optionally substituted benzothiazolyl, or optionally substituted tetrahydropyrimidinyl.

In still other embodiments of formula I or formula II wherein n is 2, $R^7$ and $R^8$ together with the nitrogen to which they are attached may form an amidinyl group, while in yet other embodiments $R^7$ and $R^8$ together with the nitrogen to which they are attached may form a guanidinyl group.

In further embodiments of formula I or formula II wherein n is 2, $R^5$ and $R^6$ together with the nitrogen to which they are attached may form =$NR^f$ wherein $R^f$ is hydrogen, and wherein $R^7$ and $R^8$ are hydrogen.

In still further embodiments of formula I or formula II wherein n is 2, one of $R^7$ and $R^8$ and one of $R^5$ and $R^6$ together with the atoms to which they are attached may form an imidazolinyl ring.

In certain embodiments of the invention, the compounds of formula I or formula II have n equal to 3. In such embodiments $R^7$ and $R^8$ may both be hydrogen, or aternatively one of $R^7$ and $R^8$ may be hydrogen while the other is alkyl, preferably methyl.

In many embodiments of formula I or formula II wherein n is 3, $R^5$ and $R^6$ may be hydrogen.

In other embodiments of formula I or formula II wherein n is 3, one of $R^7$ and $R^8$ is hydrogen and the other may be optionally substituted heteroaryl such as optionally substituted imidazolinyl, optionally substituted pyrimidinyl, optionally substituted pyrrolyl, optionally substituted imidazolyl, optionally substituted benzothiazolyl, or optionally substituted tetrahydropyrimidinyl.

In still other embodiments of formula I or formula II wherein n is 3, $R^7$ and $R^8$ together with the nitrogen to which they are attached may form an amidinyl group, while in yet other embodiments $R^7$ and $R^8$ together with the nitrogen to which they are attached may form a guanidinyl group.

In further embodiments of formula I or formula II wherein n is 3, $R^3$ and $R^4$ together with the nitrogen to which they are attached may form =$NR^f$ wherein $R^f$ is hydrogen, and wherein $R^5$ and $R^6$ are hydrogen. In still further embodiments of formula I or formula II wherein n is 2, one of $R^7$ and $R^8$ and one of $R^5$ and $R^6$ together with the atoms to which they are attached may form an imidazolinyl ring.

In certain embdodiments of formula I or formula II, $R^2$ may be aminoalkyl, alkylaminoalkyl, dialkylaminoalkyl, imidazolinylaminoalkyl, imidazolinylalkyl, guanidinylalkyl, tetrahydropyrimidinylaminoalkyl, amidinylalkyl, urealkyl or pyrimidinylaminoalkyl.

In certain embdodiments of formula I or formula II, $R^2$ may be

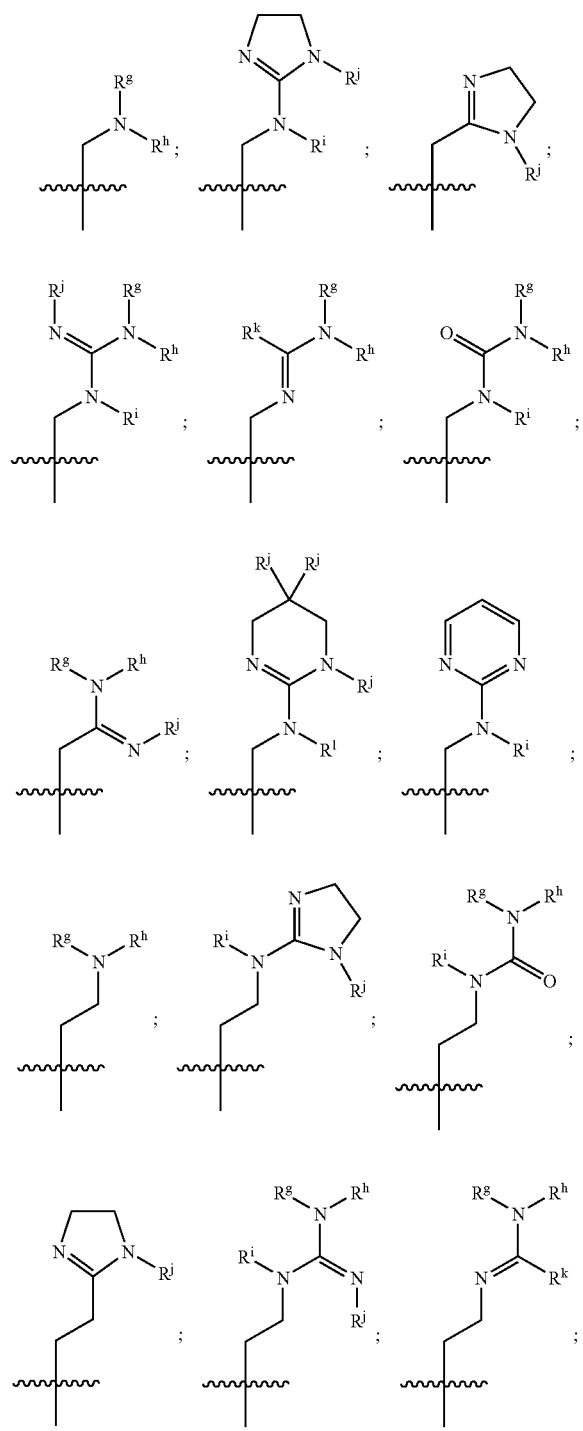

-continued

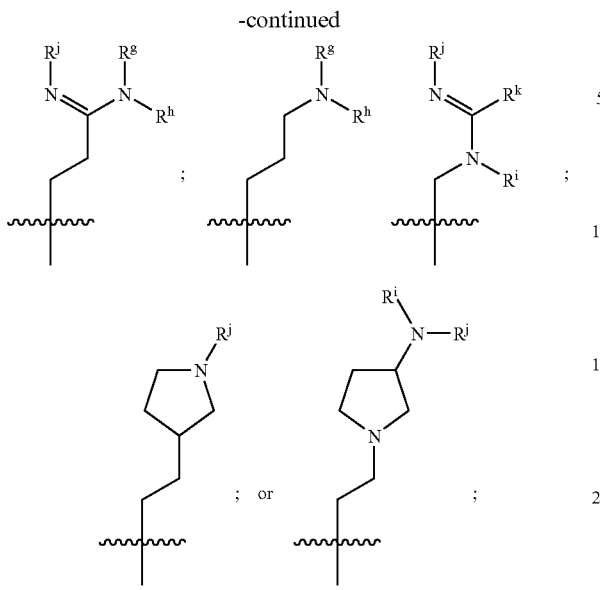

wherein $R^g$ is hydrogen, alkyl, optionally substituted phenyl or optionally substituted pyrimidinyl, and $R^h$, $R^i$, $R^j$ and $R^k$ in each independent occurrence is hydrogen or alkyl. In more specific embodiments, $R^g$, $R^h$, $R^i$ and $R^j$ are hydrogen, and $R^k$ is methyl. In still more specific embodiments, $R^2$ may be

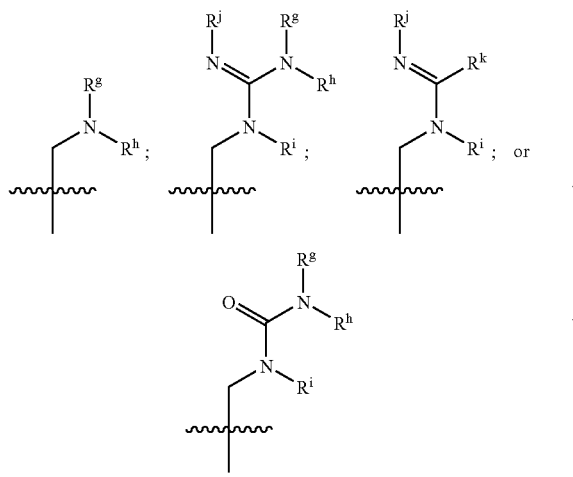

wherein $R^g$, $R^h$, $R^i$ and $R^j$ are hydrogen or methyl. More preferably, $R^2$ is

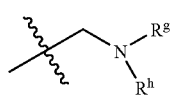

wherein $R^g$ and $R^h$ are as defined herein.

In certain embodiments of the invention, the subject compounds may be of the formula III:

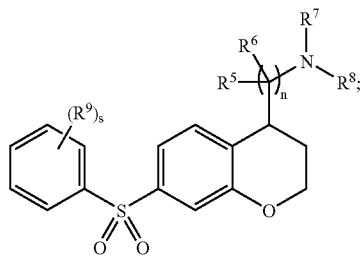

wherein:
s is from 0 to 4;
each $R^9$ is independently halo, alkyl, alkoxy, haloalkyl, heteroalkyl, cyano, —S(O)$_r$—$R^a$, —C(=O)—NR$^b$R$^c$, —SO$_2$—NR$^b$R$^c$, —N(R$^d$)—C(=O)R$^e$, or —C(=O)—R$^e$, where r is from 0 to 2, $R^a$, $R^b$, $R^c$, $R^d$ and $R^e$ each independently is hydrogen or alkyl, and $R^f$ is hydrogen, alkyl, alkoxy or hydroxy; and
n, $R^3$, $R^4$, $R^5$ and $R^6$ are as recited in claim 1.

In many embodiments of formula III, s is from 0 to 2, and each $R^9$ is independently halo, alkyl, alkoxy, or haloalkyl. In certain embodiments of formula III, n is 1 or 2, and preferably n is 1. In certain embodiments of formula III, $R^5$ and $R^6$ are hydrogen. In some embodiments of formula III wherein $R^5$ and $R^6$ are hydrogen, $R^7$ and $R^8$ are hydrogen. In other embodiments of formula III wherein $R^5$ and $R^6$ are hydrogen, one of $R^7$ and $R^8$ is hydrogen and the other is alkyl, preferably methyl. In still other embodiments of formula III wherein $R^5$ and $R^6$ are hydrogen, $R^7$ and $R^8$ may both be alkyl, preferably methyl.

In certain embodiments of the invention, the subject compounds may be more specifically of formula IV:

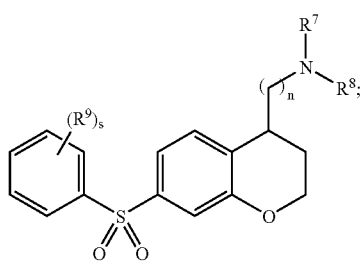

wherein:
n is 1 or 2;
s is 0 or 1;
$R^9$ is halo, alkyl, alkoxy, or haloalkyl; and
$R^5$ and $R^6$ each independently is hydrogen or alkyl, or or $R^5$ and $R^6$ together with the nitrogen to which they are attached may form an amidinyl group or a guanidinyl group.

In many embodiments of formula IV, s is from 0 to 2, and each $R^9$ is independently halo, alkyl, alkoxy, or haloalkyl. In certain embodiments of formula IV, n is 1 or 2, and preferably n is 1. In certain embodiments of formula IV, $R^7$ and $R^8$ are hydrogen. In other embodiments of formula IV, one of $R^7$ and $R^8$ is hydrogen and the other is alkyl, preferably methyl. In still other embodiments of formula IV, $R^7$ and $R^8$ may both be alkyl, preferably methyl.

Where any of $R^1, R^2, R^3, R^4, R^5, R^6, R^7, R^a, R^b, R^c, R^d, R^e, R^f, R^g, R^h, R^i, R^j$, and $R^k$ herein are alkyl or contain an alkyl moiety, such alkyl is preferably lower alkyl, i.e. $C_1$-$C_6$alkyl, and more preferably $C_1$-$C_4$alkyl.

In embodiments of the invention wherein $R^7$ and $R^8$ together with the nitrogen to which they are attached form an amidinyl, such amidinyl is of the formula:

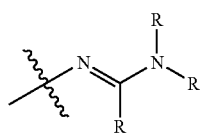

wherein each R independently is hydrogen or alkyl as defined herein.

Representative compounds in accordance with the invention are shown in the Experimental section below.

Another aspect of the invention provides a composition comprising a therapeutically effective amount of at least one compound of formula (I) and a pharmaceutically acceptable carrier.

Yet another aspect of the invention provides a method for treating a central nervous system (CNS) disease state in a subject comprising administering to the subject a therapeutically effective amount of a compound of formula I. The disease state may comprise, for example, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a compound of formula (I).

Another aspect of the present invention provides a method for producing a compound of formula (I).

Representative compounds in accordance with the invention are shown in Table 1.

TABLE 1

| # | Structure | Name | MP or M+H |
|---|---|---|---|
| 1 | 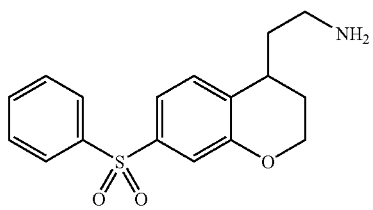 | 2-(7-Benzenesulfonyl-chroman-4-yl)-ethylamine | 244.0-245.8° C. (HCl salt) |
| 2 | 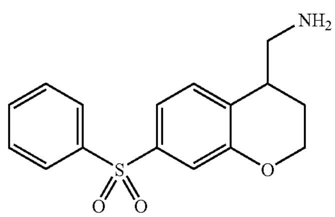 | C-(7-Benzenesulfonyl-chroman-4-yl)-methylamine | 246.8-249.8° C. (HCl salt) |
| 3 | 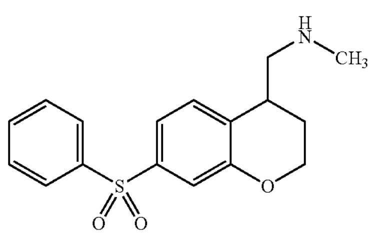 | (7-Benzenesulfonyl-chroman-4-ylmethyl)-methyl-amine | 158.1-159.8° C. (HCl salt) |
| 4 | 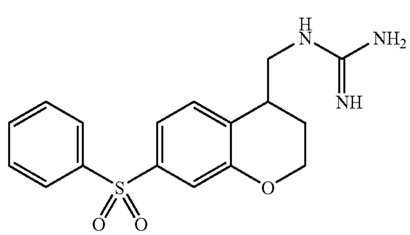 | N-(7-Benzenesulfonyl-chroman-4-ylmethyl)-guanidine | >300° C. |

TABLE 1-continued

| # | Structure | Name | MP or M+H |
|---|---|---|---|
| 5 | 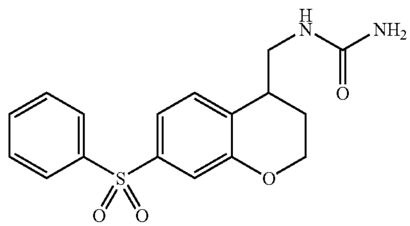 | (7-Benzenesulfonyl-chroman-4-ylmethyl)-urea | 166.2-170.9° C. |
| 6 | 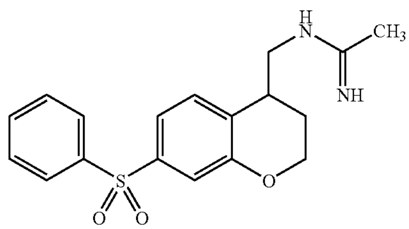 | N-(7-Benzenesulfonyl-chroman-4-ylmethyl)-acetamidine | 253.4-256.0° C. (HCl salt) |
| 7 | 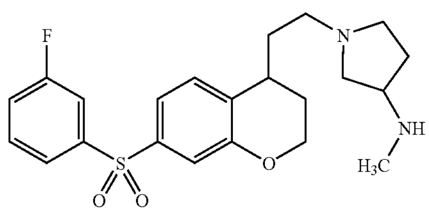 | (1-{2-[7-(3-Fluoro-benzenesulfonyl)-chroman-4-yl]-ethyl}-pyrrolidin-3-yl)-methyl-amine | 401 |
| 8 | 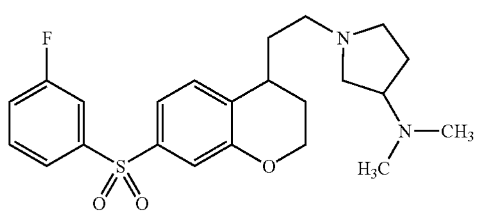 | (1-{2-[7-(3-Fluoro-benzenesulfonyl)-chroman-4-yl]-ethyl}-pyrrolidin-3-yl)-dimethyl-amine | 415 |
| 9 | 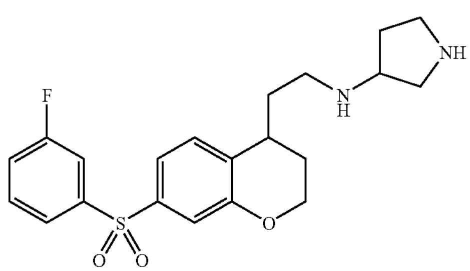 | {2-[7-(3-Fluoro-benzenesulfonyl)-chroman-4-yl]-ethyl}-pyrrolidin-3-yl-amine | 405 |
| 10 | 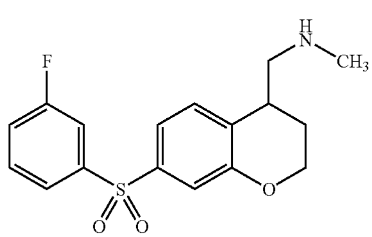 | [7-(3-Fluoro-benzenesulfonyl)-chroman-4-ylmethyl]-methyl-amine | 336 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 2004, Volumes 1-56. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein Ar, m, p, q, $R^1$, $R^2$ and $R^3$ are as defined herein. Numerous synthetic routes to the chroman and dihydrobenzofuran compounds of the invention are possible, and the procedure of Scheme A is only exemplary. A specific example of the procedure of Scheme A are provided in the following Experimental section.

In step 1a of Scheme A, ketone compound a undergoes a cyanylation reaction by treatment with diethyl cyanophosphonate to give an arylsulfonyl nitrile compound b. Ketone compound may comprise, for example, an arylsulfonyl dihydrobenzofuranone where q is 2 and p 1, an arylsulfonyl chromanone where q is 2 and p is 2, or like ketone in accordance with the invention. Corresponding, arylsulfanyl (q=0) and arylsulfinyl (q=1) ketone compounds may be used in this step, and subject to subsequent oxidation of the sulfur atom if desired. Ketone compounds a may be prepared by a variety of techniques known in the art, and specific examples of preparing such compounds are provided below in the Experimental section of this disclosure.

In step 2a, arylsulfonyl nitrile compound b is subject to reduction to provide arylsulfonyl aminomethyl compound c. This reduction removes a residual unsaturation resulting from step 1, and may be carried out using borane under polar protic solvent conditions. Compound b is a compound of formula I in accordance with the invention.

In an alternate procedure, step 1b may be carried out instead of step 1a. In step 1b, ketone compound a is treated with diethylcyanomethyl phosphonate to afford nitrile compound d. In subsequent step 2b, reduction of nitrile compound d is carried out using a platinum or palladium catalyst in the presence of hydrogen to yield compound e by removing the unsaturation in the alpha position with respect to the nitrile group of compound d. Compound e is then subject to brorane reduction in step 3b to yield arylsulfonyl aminoethyl compound f. Compound f is a compound of formula I in accordance with the invention.

Many variations on the procedure of Scheme A are possible and will suggest themselves to those skilled in the art. In one such variation, the nitrile group of compound b or e may be subject to acid hydrolysis, followed by treatment with ammonia, to yield corresponding compounds having an amidine functionality in place of the nitrile group.

Referring to Scheme B, another synthetic route for the subject compounds is shown, wherein X is a leaving group and may be the same or different in each occurrence, R is any

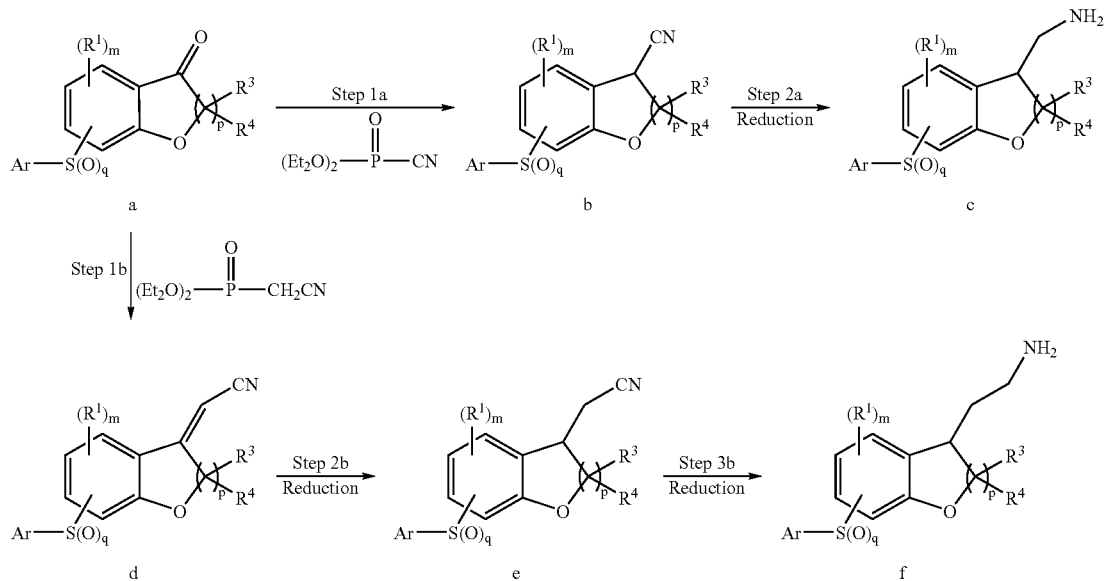

SCHEME A lower alkyl and may be the same or different in each occurrence, and Ar, m, n, p, q, $R^1$, $R^3$, $R^4$, $R^5$, $R^6$, $R^7$ and $R^8$ are as defined herein.

SCHEME B

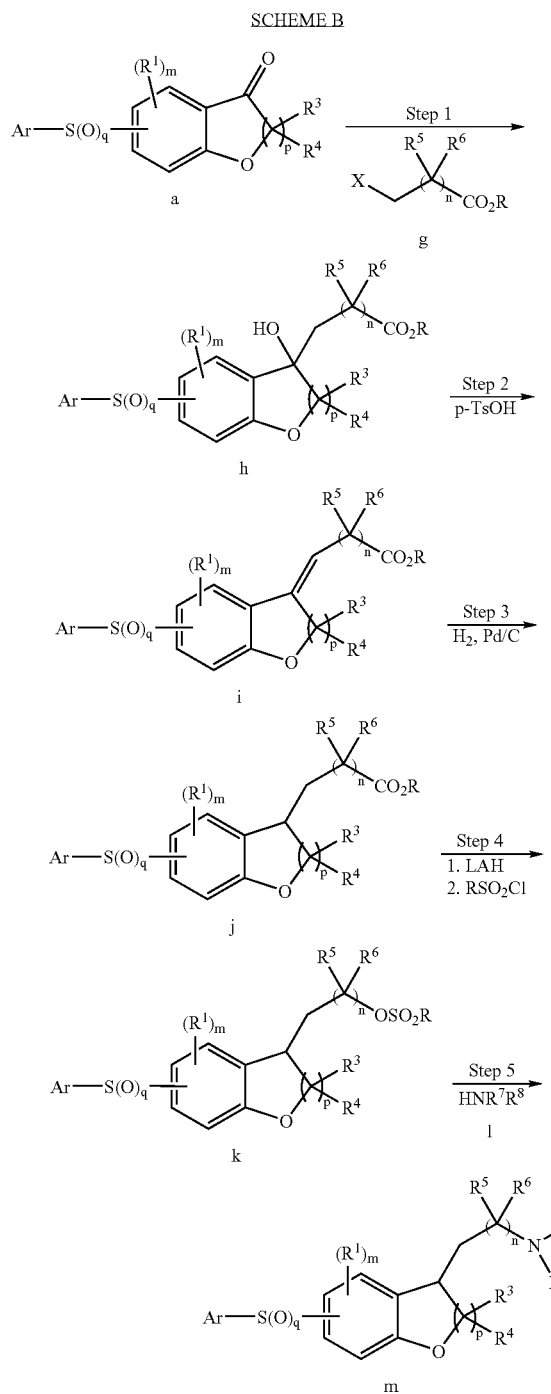

In step 1 of Scheme B, ketone compound a is subject to an alkylation reaction by treatment with a haloalkyl ester compound g to afford a hydroxy ester compound h. Ketone compound a may be any one of a variety of arylsulfonyl, arylsulfanyl or arylsulfinyl indanone and tetralinone compounds as noted above. Alkylation in step 1 may be effected by treatment of ketone compound a with zinc and iodine, followed by haloalkyl ester compound g, which may be ethyl bromopropionate (where X is bromo, n is 1, $R^3$ and $R^4$ are hydrogen, and R is ethyl), or the like.

In step 2, hydroxy ester compound h is dehydrated by treatment with acid such as para-toluenesulfonic acid, to yield an unsaturated ester compound i. In certain embodiments the dehydration of step 2 may occur spontaneously during step 1, and thus step 2 may be omitted.

A reduction reaction takes place in step 3 in which the residual unsaturation in compound i is hydrogenated by treatment with hydrogen in the presence of a suitable platinum or palladium catalyst, to provide ester compound j.

In step 4, the compound j is subject to reduction, followed by alkylsulfonylation, to afford sulfonate compound k. This step may be carried out by treatment of compound j with reducing agent such as lithium aluminum hydride to form an alcohol (not shown), which is then treated with alkylsulfonyl halide such as methanesulfonyl chloride.

Amination of arylsulfonate compound k in step 5 provides amine compound m. This amination in many embodiments may comprise treatment of sulfonate compound k with amine l. For a compound m where $R^7$ and $R^8$ are hydrogen, compound k may be treated with sodium azide to form an azido compound (not shown), which is then reduced, using lithium aluminum hydride or like reducing agent, followed by acid workup to yield amine m. Compound m is a compound of formula I in accordance with the invention.

As with Scheme A, many variations on the procedure of Scheme B are possible. In on such variation, sulfonate compound k may be treated with cyanide to form a nitrile compound, which in turn may be reduced to provide an amine.

Scheme C shows another synthetic route to compounds of the invention, wherein Ar, m, p, q, $R^1$, $R^3$, $R^4$, $R^5$, $R^6$, $R^7$ and $R^8$ are as defined herein.

SCHEME C

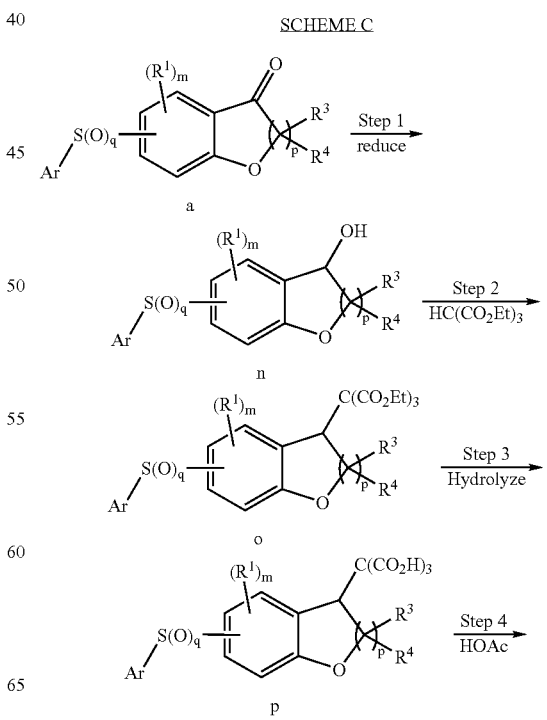

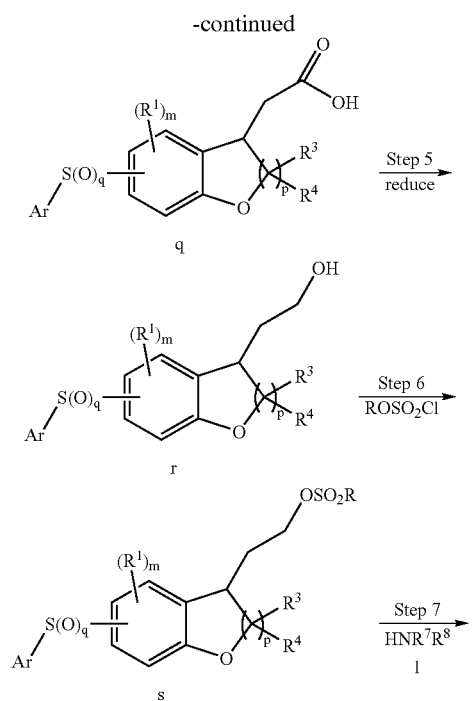

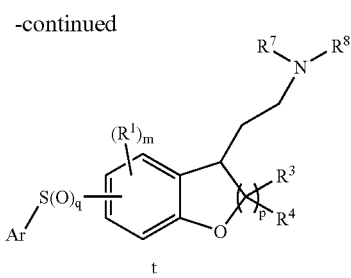

In step 1 of Scheme C, ketone a is subject to reduction to form alcohol compound n. Compound n is then treated with 2-cthoxycarbonyl-malonic acid diethyl ester in step 2 to afford triester compound o. In step 3 compound o is hydrolized to triacid compound p, which in turn is treated with acetic acid to afford acetyl compound q in step 4. The acetyl compound is reduced to alcohol r in step 5. In step 6 the alcohol r undergoes alkylsulfonylation to afford alkylsulfonyl compound s. Compound s may then be reacted with amine l to provide amino compound t, which is a compound of formula I in accordance with the invention.

The amino functionality of the subject compounds may be subject to further reaction to afford monoalkylamino, dialkylamino, amidinyl, guanidinyl, imidazolinyl, imidazolinylamino, and other functionalities as shown in Scheme D.

SCHEME D

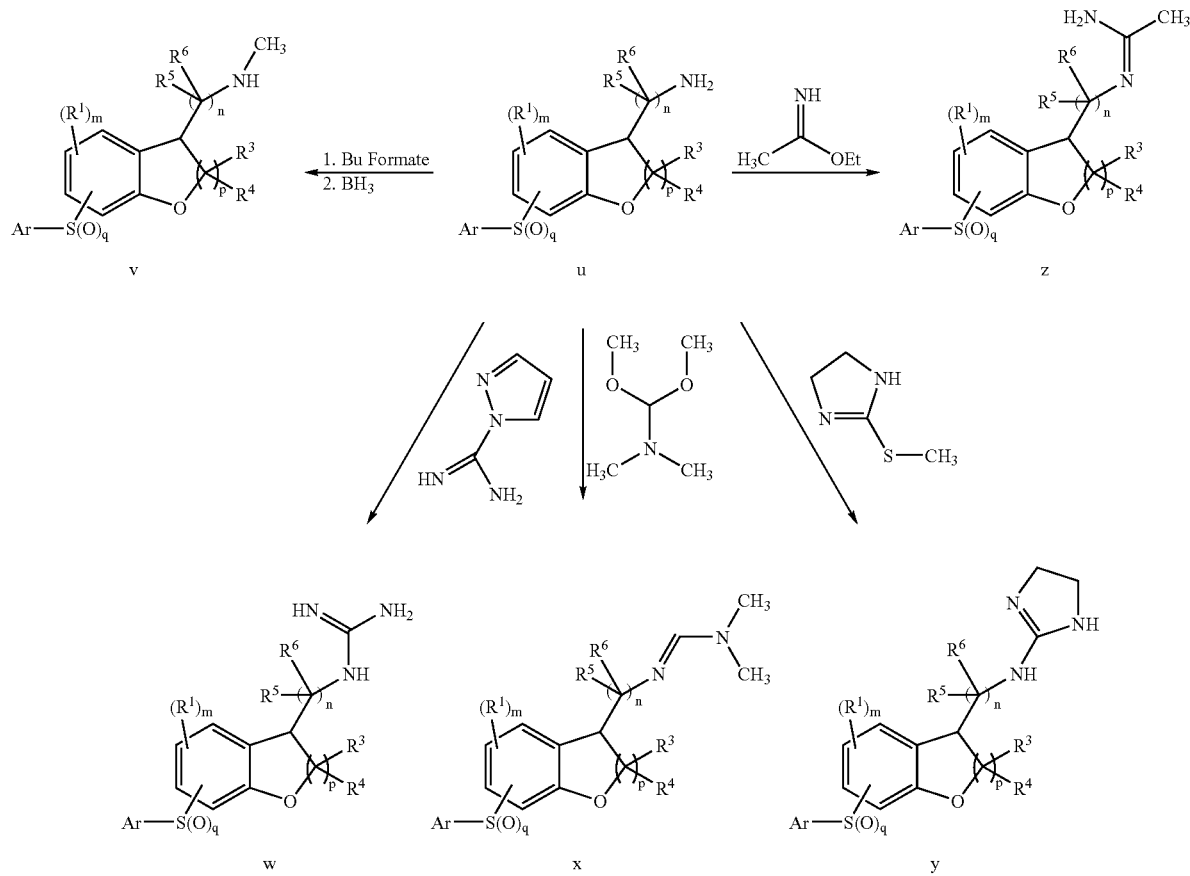

In Scheme C, arylsulfonyl amine compound u may be converted to a formamide which is then reduced to provide methylamino compound v.

Compound u may also be reacted with 1H-pyrazol-1-carboxamidine hydrochloride in the presence of amine catalyst under polar aprotic solvent conditions to afford urea compound w. Alternatively, compound u may be reacted with dimethylformamide dimethyl acetal to yield acetamidine compound x. As yet another alternative, compound u may be treated with 2-methylsulfanyl-4,5-dihydro-1H-imidazole to afford imidazolinylamino compound y. In still another alternative, compound u may be reacted with ethyl imidate (acetimidic acid ethyl ester) to provide acetamidine compound z.

Specific details for producing compounds of formula I are described in the Examples section below.

Utility

The compounds of the invention have selective affinity for 5-HT receptors, including the 5-HT$_6$ the 5-HT$_{2A}$ receptor, or both, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor in radioligand binding, FLIPR and functional assays are described below.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

Step 1 3-(3-Fluoro-phenoxy)-propionic acid

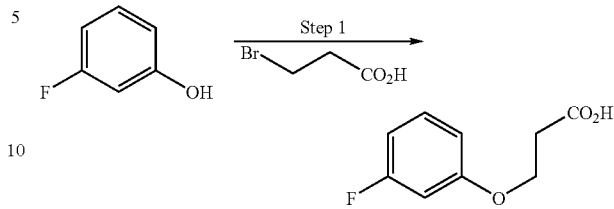

3-Fluorophenol (8.9 g, 79.5 mmol) and 3-bromopropionic acid (12.24 g, 80.0 mmol) were placed in a flask. A solution of NaOH (6.7 g, 167 mmol) in 20 mL water was added slowly to the flask. The reaction mixture was heated to reflux for two hours and then cooled to room temperature and partitioned between ethyl acetate and water. The organic layer was dried over $MgSO_4$, and solvent was evaporated under reduced pressure to give 4.57 g (25 mmol, 31.4%) of 3-(3-fluoro-phenoxy)-propionic acid. MS: 185 $(M+H)^+$.

Step 2 7-Fluoro-chroman-4-one

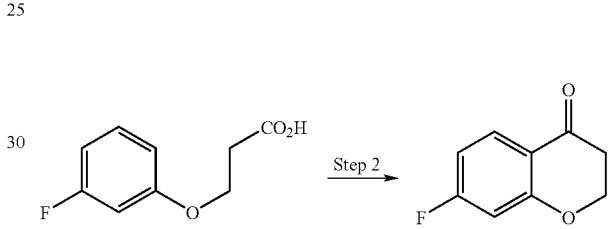

3-(3-Fluoro-phenoxy)-propionic acid (3.37 g, 18.3 mmol), was dissolved in a mixture of 25 mL trifluoroacetic acid and 9 mL methanesulfonic acid. The reaction mixture was hteated to 90° C. and was stirred at 90° C. for one hour. The reaction mixture was cooled to room temperature and partitioned between ethyl acetate and water. The organic layer was dried over $MgSO_4$, and solvent was evaporated under reduced pressure. The residue was eluted through silica gel (15% EtOAc in hexanes), and solvent was removed under reduced pressure to yield 1.24 g (7.5 mmol, 41%) of 7-fluoroo-chroman-4-one (MS: 167 $(M+H)^+$.

Step 3 7-Phenylsulfanyl-chroman-4-one

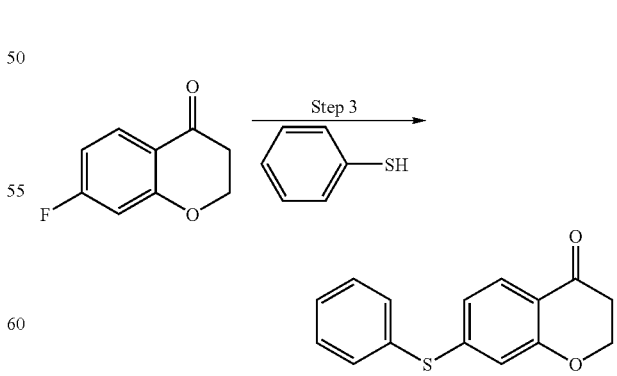

A solution of 7-fluoroo-chroman-4-one (1.87 g, 11.27 mmol) and $K_2CO_3$ (9.28 g, 67.12 mmol) was added to 20 mL of dimethylformamide (DMF). Benzenethiol (1.37 mL, 13.52 mmol) was added, and the reaction mixture was stirred at

ABBREVIATIONS

| | |
|---|---|
| DCM | dichloromethane/methylene chloride |
| DMF | N,N-dimethylformamide |
| DMAP | 4-dimethylaminopyridine |
| EtOAc | ethyl acetate |
| EtOH | ethanol |
| tBuOH | tert-butanol |
| gc | gas chromatography |
| HMPA | hexamethylphosphoramide |
| HOAc/AcOH | acetic acid |
| hplc | high performance liquid chromatography |
| mCPBA | m-chloroperbenzoic acid |
| MeCN | acetonitrile |
| NMP | N-methyl pyrrolidinone |
| TEA | triethylamine |
| TFA | trifluoroacetic acid |
| THF | tetrahydrofuran |
| LDA | lithium diisopropylamine |
| TLC | thin layer chromatography |

Preparation 1

7-Benzenesulfonyl-chroman-4-one

The synthetic procedure described in this Preparation was carried out according to the process shown in Scheme E.

SCHEME E

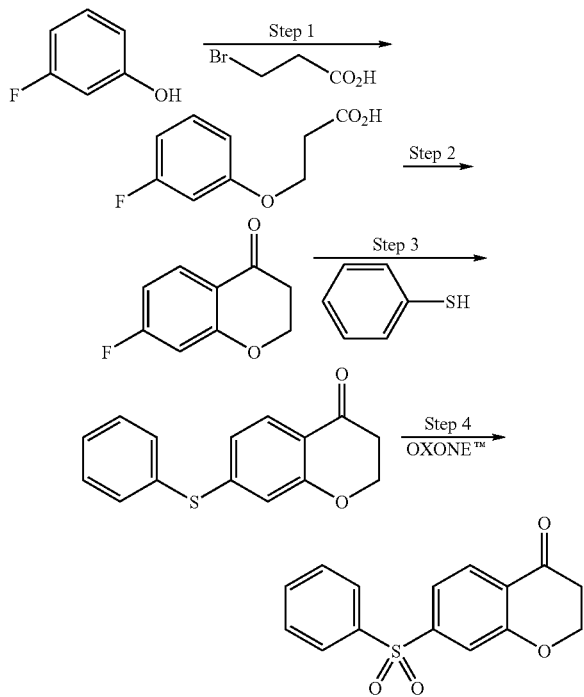

room temperature for two hours, and then partitioned between ethyl acetate and water. The organic layer was dried over MgSO$_4$, and solvent was evaporated under reduced pressure to yield an oil that was eluted through silica gel using hexanes/EtOAc (9:1). Removal of solvent under reduced pressure provided 2.21 g (8.62 mmol, 77%) of 7-phenylsulfanyl-chroman-4-one. MS: 257 (M+H)$^+$.

Step 4 7-Benzenesulfonyl-chroman-4-one

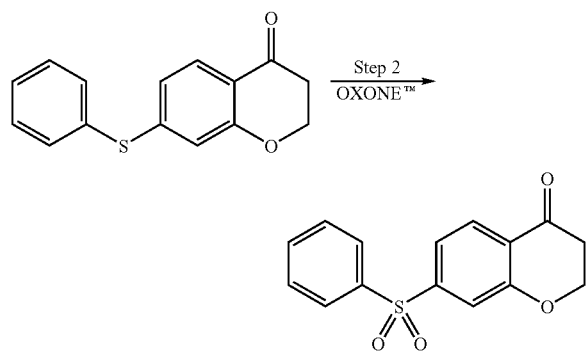

A solution of 7-phenylsulfanyl-chroman-4-one (2.21 g, 8.62 mmol) in 20 mL o MeOH and 2 mL water was stirred at room temperature. OXONE™ (potassium peroxymonosulfate, 6.35 g, 10.35 mmol) was added, and the reaction mixture was stirred for 3 hours at room temperature. The reaction mixture was partitioned between ethyl acetate and water. The organic layer was dried over MgSO$_4$, and solvent was evaporated under reduced pressure. The resulting residue was eluted through silica gel with 35% EtOAc in hexanes. Removal of solvent under reduced pressure afforded 1.56 g (5.41 mmol, 63%) of 7-benzenesulfonyl-chroman-4-one. MS: 289 (M+H)$^+$.

Preparation 2

7-Benzenesulfonyl-2,2-dimethyl-chroman-4-one

The synthetic procedure described in this Preparation was carried out according to the process shown in Scheme F.

SCHEME F

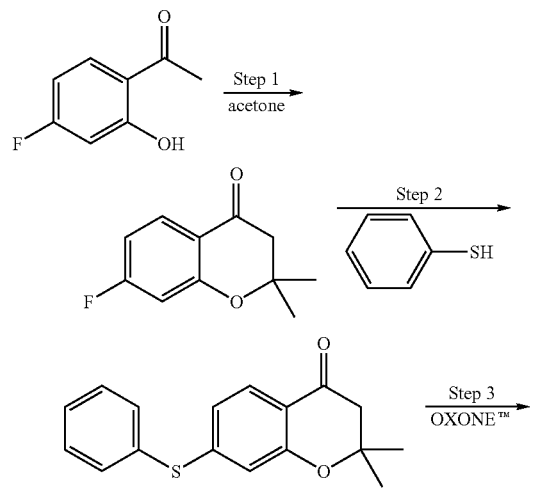

-continued

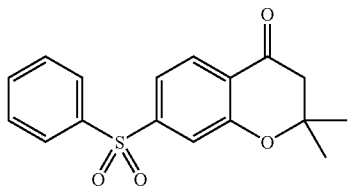

Step 1 7-Fluoro-2,2-dimethyl-chroman-4-one

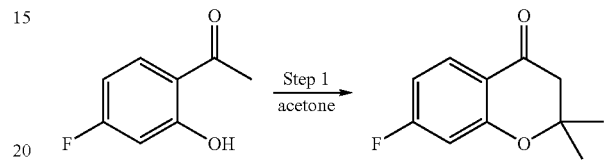

1-(4-Fluoro-2-hydroxy-phenyl)-ethanone (5.0 g, 32.44 mmol), acetone (11.92 mL, 162.2 mmol) and pyrrolidine (2.7 mL, 32.44 mmol) were dissolved in 20 mL benzene, and the reaction mixture was refluxed for four hours. The reaction mixture was cooled to room temperature and partitioned between ethyl acetate and 1 N HCl. The organic layer was dried over MgSO$_4$, and solvent was evaporated under reduced pressure. The resulting residue was chromatographed (15% ethyl acetate in hexanes eluting through silica) and solvent was removed to yield 3.33 g (17.16 mg, 53%) of 7-fluoro-2,2-dimethyl-chroman-4-one as an oil. MS: 195 (M+H)$^+$.

Step 2
7-Benzenesulfanyl-2,2-dimethyl-chroman-4-one

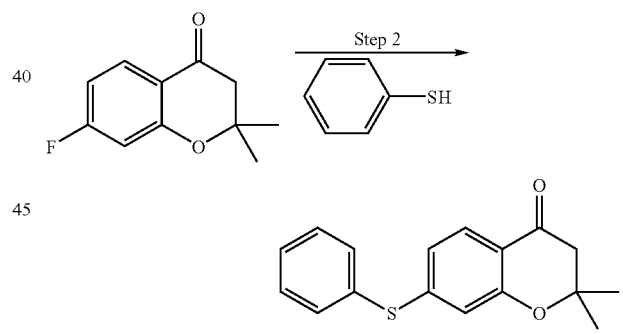

The procedure of step 3 of preparation 1 was used to provide 1.49 g of 7-Benzenesulfanyl-2,2-dimethyl-chroman-4-one. MS: 285 (M+H)$^+$.

Step 3
7-Benzenesulfonyl-2,2-dimethyl-chroman-4-one

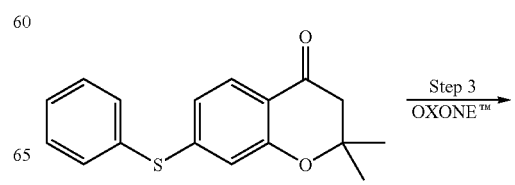

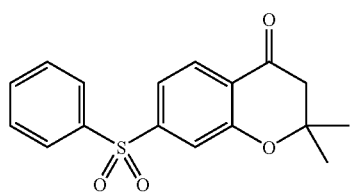

The procedure of step 4 of preparation 1 was used to provide 1.10 g of 7-Benzenesulfonyl-2,2-dimethyl-chroman-4-one. MS: 317 (M+H)⁺.

Example 1

C-(7-Benzenesulfonyl-chroman-4-yl)-methylamine

The synthetic procedure described in this Example was carried out according to the process shown in Scheme G.

SCHEME G

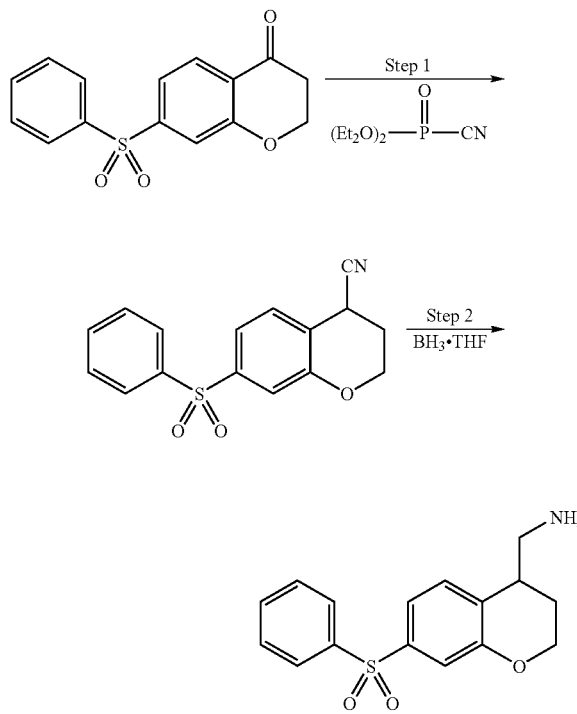

Step 1 7-Benzenesulfonyl-chroman-4-carbonitrile

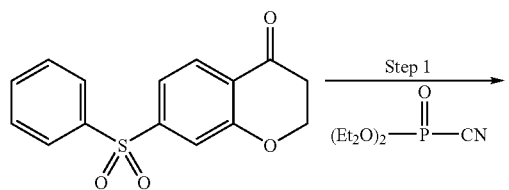

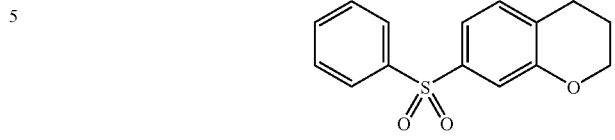

7-Benzenesulfonyl-chroman-4-one from Preparation 1 above (500 mg, 1.73 mmol) was dissolved in 10 mL of tetrahydrofuran (THF). Diethyl cyanophosphonate (789 uL, 5.21 mmol) and lithium cyanide (10.42 mL, 5.21 mmol) were added, and the reaction mixture was stirred for 10 minutes at room temperature. Water (150 (mL) was added, and the aqueous mixture was extracted twice with 200 mL of EtOAc. The combined organic layers were washed with brine, dried over MgSO$_4$, and the solvent was evaporated under reduced pressure. The residue was dissolved in 5 mL THF, and 70 mL of MeOH was added. SmI$_2$ (52 mL, 5.21 mmol) was then added over five minutes, and the reaction mixture was stirred for 10 minutes at room temperature. The reaction was quenched by addition of 20 mL 1 N HCl, and the resulting aqueous mixture was extracted with EtOAc and 1 N Na$_2$S$_2$O$_3$. The organic phase was dried over MgSO$^4$, and solvent was removed under reduced pressure. The residue eluted through silica gel using 40% EtOAc in hexanes, and solvent was removed under reduced pressure to yield 300 mg (1 mmol, 58%) of 7-benzenesulfonyl-chroman-4-carbonitrile. MS: 300 (M+H)⁺.

Step 2
C-(7-Benzenesulfonyl-chroman-4-yl)-methylamine

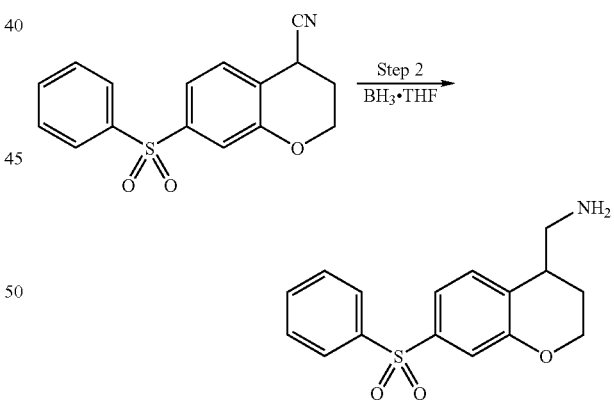

7-Benzenesulfonyl-chroman-4-carbonitrile (300 mg, 1 mmol) was dissolved in 10 mL THF, and 237 ul (2.5 mmol) of BH$_3$.DMF was added. The reaction mixture was stirred for one hour at room temperature, and then heated to 80° C. for twenty minutes. The reaction mixture was then cooled, quenched by addition of methanol, and diluted with water. The aqueous mixture was extrated with EtOAc. The organic phase was dried over MgSO$_4$, and solvent was removed under reduced pressure to yield 95 mg (31%) of C-(7-benzenesulfonyl-chroman-4-yl)-methylamine. MS: 304 (M+H)⁺. This product was dissolved in 2N HCl/EtOH and recrystallized by addition of Et2O to afford 52 mg of the corresponding hydrochloride salt. Mp: 246.8-249.8° C.

Example 2

2-(7-Benzenesulfonyl-chroman-4-yl)-ethylamine

The synthetic procedure described in this Example was carried out according to the process shown in Scheme H.

SCHEME H

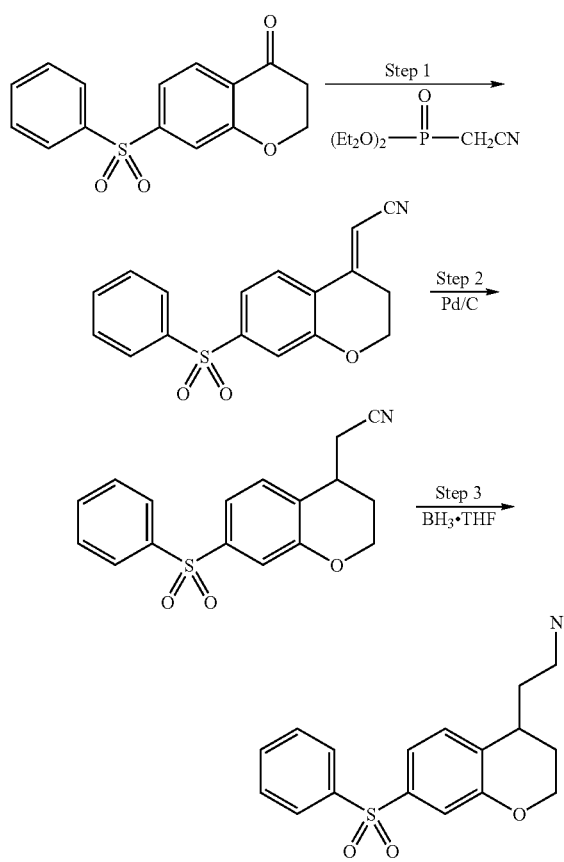

Step 1
(7-Benzenesulfonyl-chroman-4-ylidene)-acetonitrile

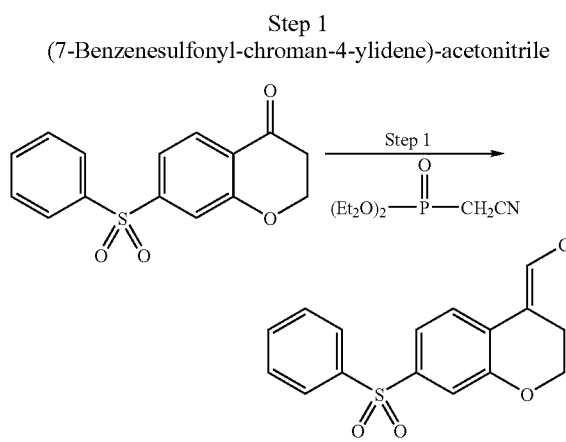

Sodium hydride (90 mg, 3.91 mmol) was added to 10 mL THF and was stirred for 30 minutes at 0° C. 7-Benzenesulfonyl-chroman-4-one (564 mg, 1.96 mmol) was dissolved in 5 mL THF, and the resulting solution was added to the reaction mixture. The reaction mixture was stirred for 10 minutes and then quenched by addition of 150 mL water. The resulting aqueous mixture was extracted twice with 200 mL EtOAc. The combined organic layers were dried over MgSO$_4$, and solvent was removed under reduced pressure. The residue was chromatographed through silica gel using 35% EtOAc in hexanes, and solvent was removed under reduced pressure to afford 395 mg (1.27 mmol, 65%) of (7-benzenesulfonyl-chroman-4-ylidene)-acetonitrile. MS: 312 (M+H)$^+$.

Step 2
(7-Benzenesulfonyl-chroman-4-yl)-acetonitrile

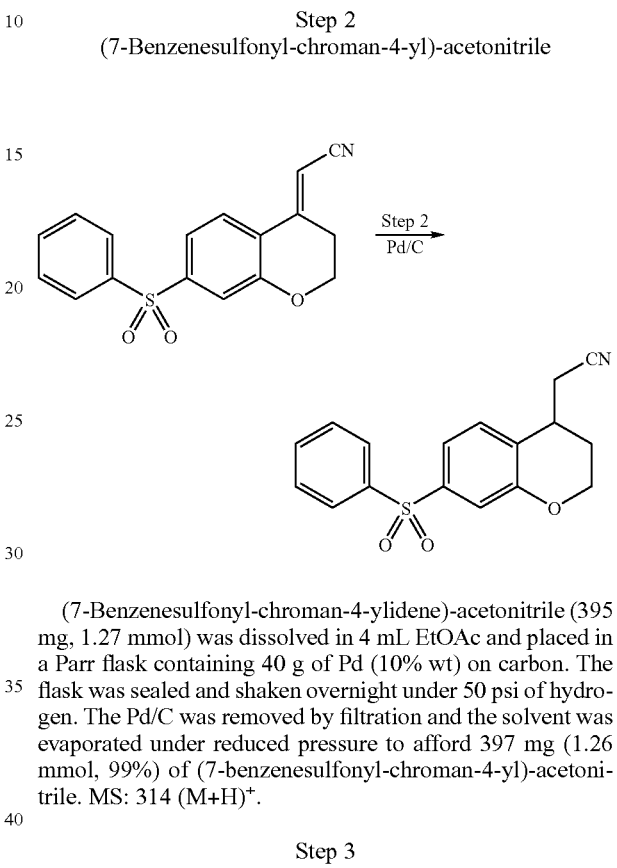

(7-Benzenesulfonyl-chroman-4-ylidene)-acetonitrile (395 mg, 1.27 mmol) was dissolved in 4 mL EtOAc and placed in a Parr flask containing 40 g of Pd (10% wt) on carbon. The flask was sealed and shaken overnight under 50 psi of hydrogen. The Pd/C was removed by filtration and the solvent was evaporated under reduced pressure to afford 397 mg (1.26 mmol, 99%) of (7-benzenesulfonyl-chroman-4-yl)-acetonitrile. MS: 314 (M+H)$^+$.

Step 3
2-(7-Benzenesulfonyl-chroman-4-yl)-ethylamine

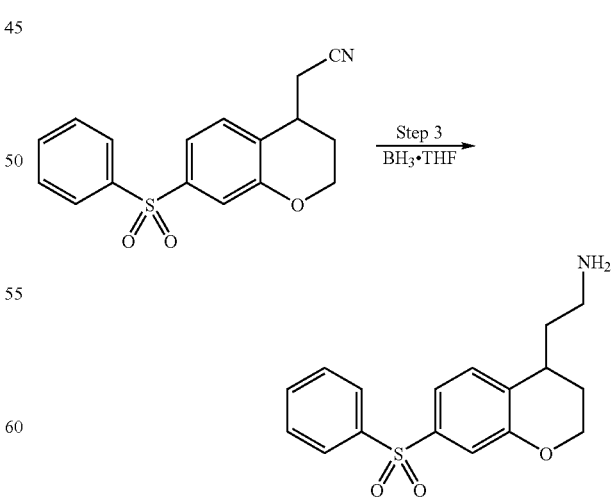

(7-Benzenesulfonyl-chroman-4-yl)-acetonitrile (397 mg, 1.26 mmol) was dissolved in 5 mL THF, and 190 ul (1.9 mmol) of BH$_3$.DMF was added. The reaction mixture was heated to reflux for one hour and then cooled to room temperature, quenched by addition of methanol, and diluted with water. The aqueous mixture was extrated with EtOAc. The organic phase was dried over MgSO₄, and solvent was removed under reduced pressure. The residue was chromatographed through silica gel (MeOH:CH₂Cl₂:NH₄OH 8%:90%:2%), and solvent was removed under reduced pressure to yield 120 mg (0.38 mmol, 30%) of 2-(7-benzenesulfonyl-chroman-4-yl)-ethylamine. This product was dissolved in 2N HCl/EtOH and recrystallized by addition of Et₂O to afford 95 mg of the corresponding hydrochloride salt. Mp: 244.6-245.8° C.

Example 3

(7-Benzenesulfonyl-chroman-4-ylmethyl)-methyl-amine

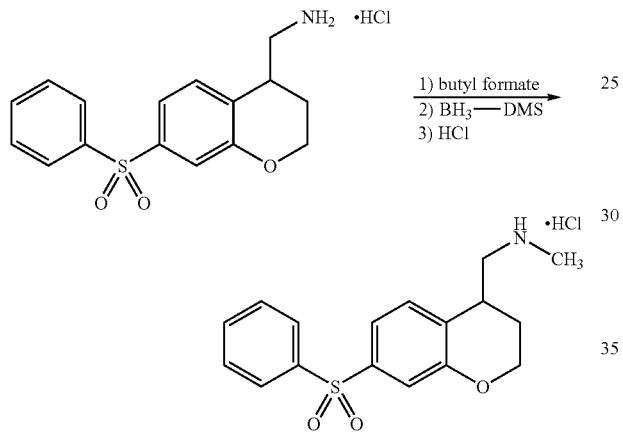

114 mg (0.376 mmol) of -(7-Benzenesulfonyl-chroman-4-yl)-methylamine HCl salt was dissolved in excess butyl formate and heated to reflux for 15 minutes. The resulting formamide was cooled to room temperature, concentrated, the residue dissloved in 3 mL THF and then reduced by adding 5 µL (1.5 eq., 0.563 mmol) of 10M BH3.DMS complex. The mixture was stirred for 1.5 h and quenched with methanol, partitioned between ethyl acetate and water, dried, concentrated and treated with 2 N HCl/EtOH and ether to provide 80 mg (60%) of (7-benzenesulfonyl-chroman-4-ylmethyl)-methyl-amine as the HCl salt, MS: 318 (M+H).

Example 4

N-(7-Benzenesulfonyl-chroman-4-ylmethyl)-guanidine

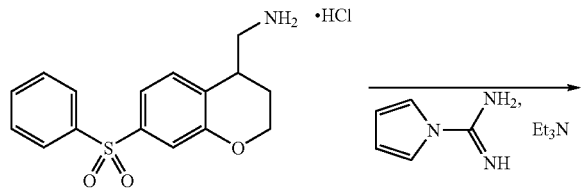

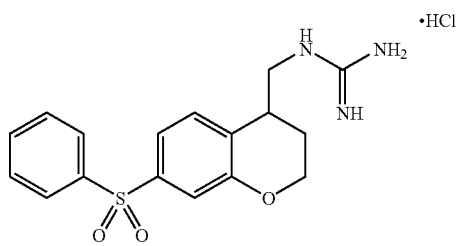

C-(7-Benzenesulfonyl-chroman-4-yl)-methylamine HCl salt (125 mg, 0.378 mmol), 1H-pyrazol-1-carboxamidine hydrochloride (65 mg, 0.44 mmol) and 62 µL of triethylamine (0.44 mmol) were dissolved in 3 mL of EtOH. The reaction mixture was heated to 60° C. overnight. The mixture was then cooled and partitioned between EtOAc and water, dried over MgSO₄ concentrated and purified column chromatography (silica gel, MeOH/CHCl₃/NH₄OH 10:89:1). Formation of the HCl salt gave 15 mg (11%) of N-(7-Benzenesulfonyl-chroman-4-ylmethyl)-guanidine HCl, MS: 346 (M+H)⁺.

Example 5

(7-Benzenesulfonyl-chroman-4-ylmethyl)-urea

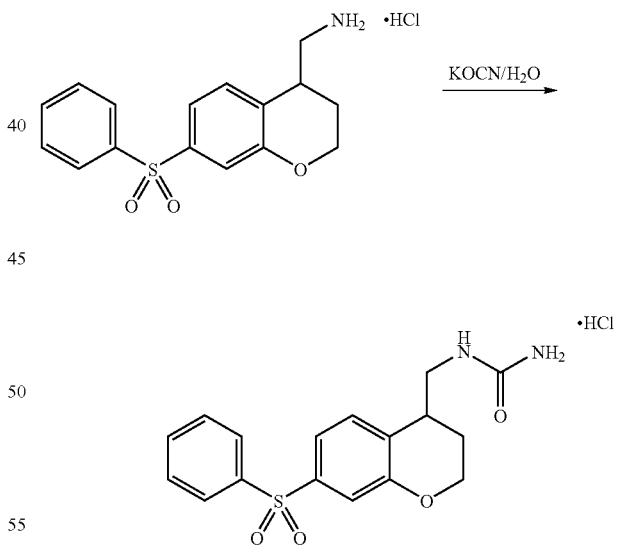

C-(7-Benzenesulfonyl-chroman-4-yl)-methylamine HCl salt (75 mg, 0.22 mmol) was dissolved in 8 mL water and KOCN (36 mg, 0.44 mmol) was added. The reaction mixture was stirred at 100° C. for 30 minutes., then cooled, partitioned between EtOAc and water, and dried over MgSO₄. After concentration, the product was precipitated from Et₂O/hexanes. After formation of the HCl salt, 24 mg (32%) of (7-Benzenesulfonyl-chroman-4-ylmethyl)-urea was collected. MS: 347 (M+H)⁺.

Example 6

N-(7-Benzenesulfonyl-chroman-4-ylmethyl)-acetamidine

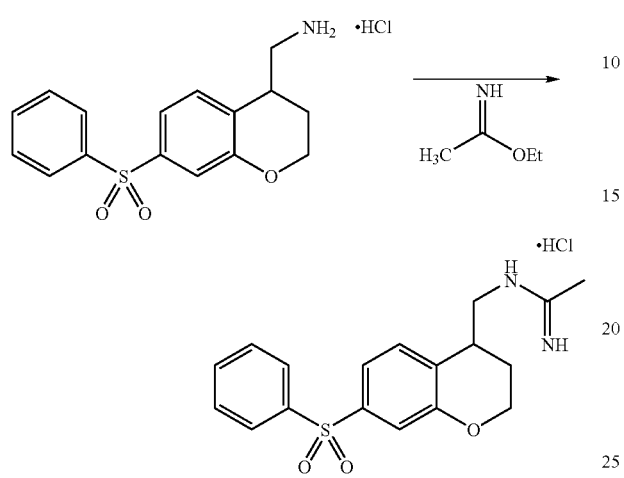

C-(7-Benzenesulfonyl-chroman-4-yl)-methylamine HCl salt (90 mg, 0.26 mmol) and methyl imidate (acetimidic acid methyl ester, 58 mg, 0.529 mmol) were dissolved in 3 mL of absolute ethanol and 0.362 mL of triethylamine (2.6 mmol) was added. The reaction mixture was stirred at 80° C. for 2 days. It was then cooled, partitioned between EtOAc and water, dried over MgSO$_4$ concentrated and purified using column chromatography (silica gel, MeOH/CHCl$_3$/NH$_4$OH 10:89:1) After formation of the HCl salt, 9 mg (10%) of. N-(7-Benzenesulfonyl-chroman-4-ylmethyl)-acetamidine was collected. MS: 345 (M+H)$^+$.

Example 7

(1-{2-[7-(3-Fluoro-benzenesulfonyl)-chroman-4-yl]-ethyl}-pyrrolidin-3-yl)-methyl-amine The synthetic procedure described in this Example was carried out according to the process shown in Scheme I.

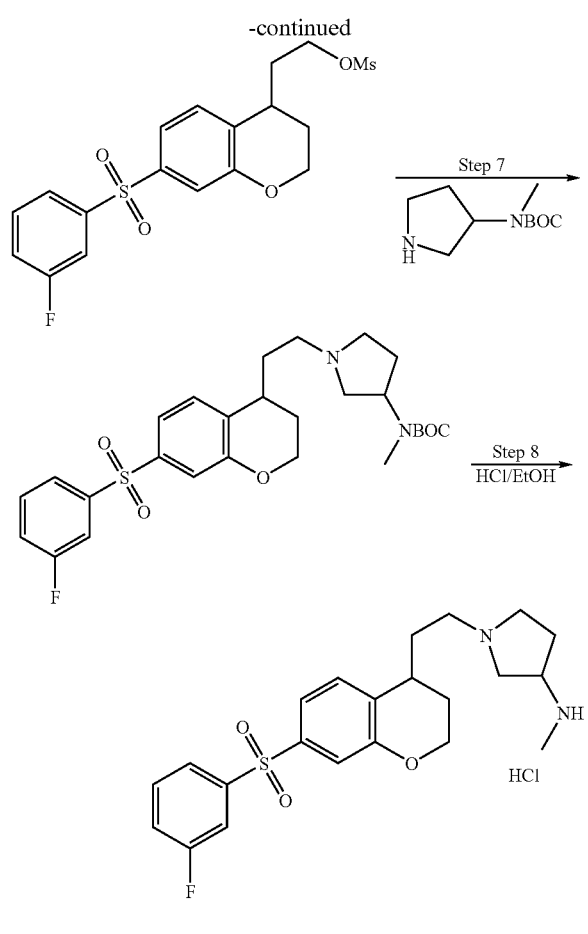

Step 1 7-(3-Fluoro-benzenesulfonyl)-chroman-4-ol

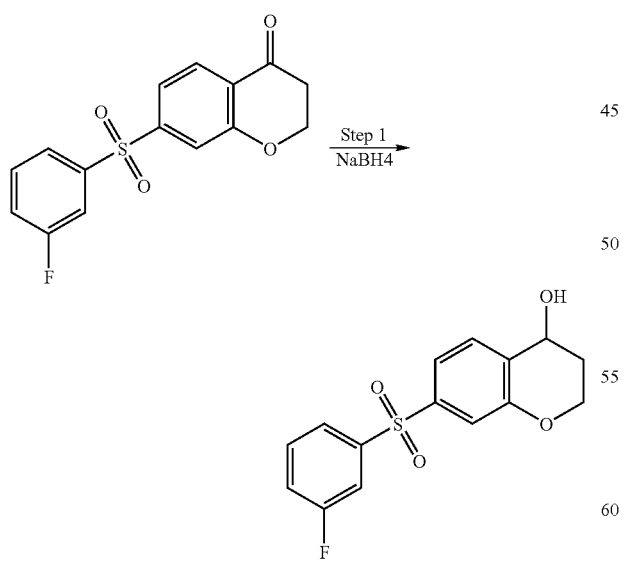

The starting material 7-(3-Fluoro-benzenesulfonyl)-chroman-4-one was synthesized by the procedure of Example 1 except that 3-fluorothiophenol was used instead of thiophenol.

To a solution of 7-(3-Fluoro-benzenesulfonyl)-chroman-4-one (3.31 g, 10.81 mmol) in THF (100 ml) was added NaBH4 (0.49 g, 12.9 mmol) at 0° C. The mixture was stirred at 0° C. for 3 hours. The reaction mixture was partitioned between water and EtOAc. The EtOAc layer was washed with brine, dried with MgSO4, filtered and concentrated. The residue was purified with flash chromatography to give 2.0 g of 7-(3-Fluorobenzene-sulfonyl)-chroman-4-ol, as a white foam. MS: 599.2 (2M−OH)+.

Step 2 2-Ethoxycarbonyl-2-[7-(3-fluoro-benzenesulfonyl)-chroman-4-yl]-malonic acid diethyl ester

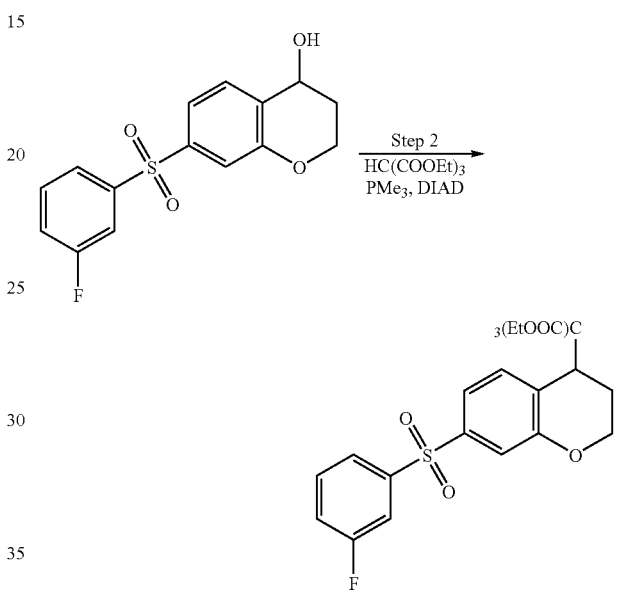

To a solution of 7-(3-Fluorobenzene-sulfonyl)-chroman-4-ol (3.0 g, 9.7 mmol) in THF (40 ml) and toluene (40 ml) was added HC(COOEt)3 (4.5 g, 19.5 mmol) and then PMe3 (19.5 ml of 1.0M THF solution). The mixture was cooled to −78° C. DIAD (4.0 g, 19.5 mmol) was added dropwise. The mixture was stirred at −78° C. for 1 hour and then at RT for overnight. The next day the TLC showed that the reaction was complete. The solvent was removed and the residue was partitioned between EtOAc and H2O. The EtOAc layer was washed with brine, dried with MgSO4, concentrated and purified with flash column to give 2-Ethoxycarbonyl-2-[7-(3-fluoro-benzenesulfonyl)-chroman-4-yl]-malonicacid diethyl ester: 5.0 g, clear oil. MS: 545 (M+Na)+.

Step 3 2-Carboxy-2-[7-(3-fluoro-benzenesulfonyl)-chroman-4-yl]-malonic acid

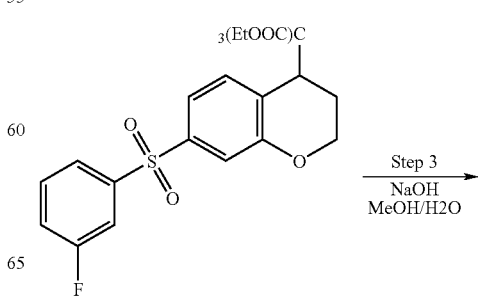

-continued

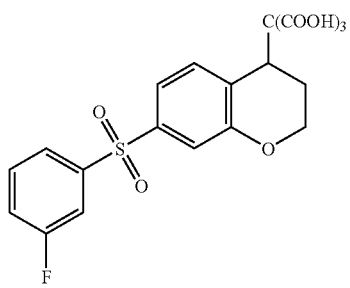

To a solution of 2-Ethoxycarbonyl-2-[7-(3-fluoro-benzenesulfonyl)-chroman-4-yl]-malonicacid diethyl ester (5.0 g, 9.6 mmol) in MeOH (50 ml) was added NaOH (25 ml, 3N in H₂O). The milky mixture was heated at 65° C. overnight. The solvent was evaporated to give crude 2-Carboxy-2-[7-(3-fluoro-benzenesulfonyl)-chroman-4-yl]-malonic acid as a solid.

Step 4
[7-(3-Fluoro-benzenesulfonyl)-chroman-4-yl]-acetic acid

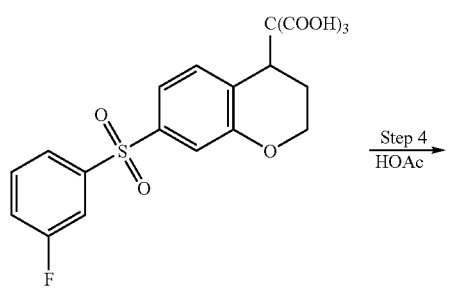

The crude 2-Carboxy-2-[7-(3-fluoro-benzenesulfonyl)-chroman-4-yl]-malonic acid of step 3 was dissolved in HOAc (50 ml), and the mixture was heated to 100° C. overnight. HOAc was removed via vacuum, and he residue was dissolved in EtOAc, washed with H₂O, brine, dried with MgSO₄, filtered and concentrated to give [7-(3-Fluoro-benzenesulfonyl)-chroman-4-yl]-acetic acid as a colorless oil which turned to a white solid upon standing: 2.55 g; MS 373(M+Na)+, 723.3 (2M+Na)+.

Step 5 2-[7-(3-Fluoro-benzenesulfonyl)-chroman-4-yl]-ethanol

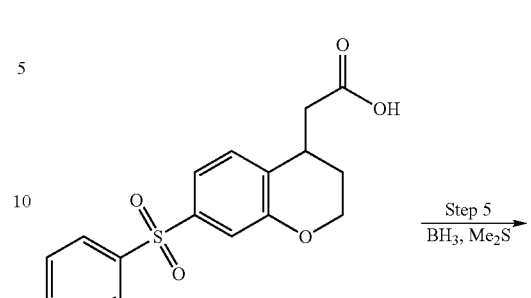

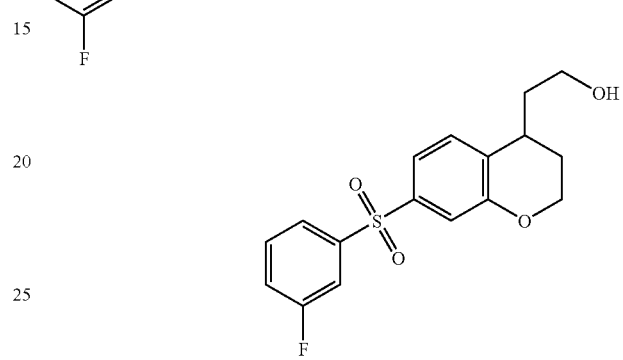

To a solution of [7-(3-Fluoro-benzenesulfonyl)-chroman-4-yl]-acetic acid (1.5 g, 4.28 mmol) in THF 40 ml) was added BH3 Me2S (0.41 ml, 4.32 mmol) at 0° C. The mixture was stirred in the ice bath for 30 minutes and then at room temperature overnight. The mixture was quenched with MeOH and the solvent was removed. The residue was dissolved in EtOAc, washed with brine, dried with MgSO4, filtered and concentrated to give 2-[7-(3-Fluoro-benzenesulfonyl)-chroman-4-yl]-ethanol as a clear syrup: 1.35 g; MS: 337.2 (M+H)+, 378.2(M+CH3CN+H)+.

Step 6 Methanesulfonic acid 2-[7-(3-fluoro-benzenesulfonyl)-chroman-4-yl]-ethyl ester

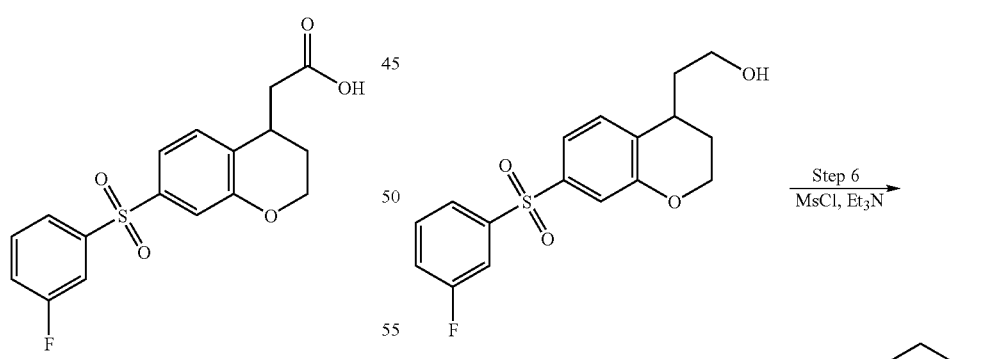

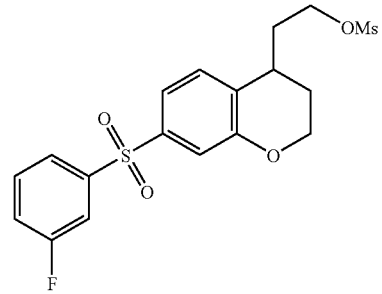

A solution of 2-[7-(3-Fluoro-benzenesulfonyl)-chroman-4-yl]-ethanol (1.35 g, 4.01 mmol) in CH₂Cl₂ (40 ml) was cooled to 0° C. Et₃N (4.06 g, 40.2 mmol) was added at 0° C. followed by methanesulfonylchloride (0.91 g, 8.00 mmol). The reaction mixture was stirred in an ice bath for 2 hours, then diluted with CH₂Cl₂, washed with brine, dried with MgSO₄, filtered and concentrated to give AN oil residue. The residue was purified with flash chromatography to give methanesulfonic acid 2-[7-(3-fluoro-benzenesulfonyl)-chroman-4-yl]-ethyl ester as a clear oil: 1.35 g; MS: 415.2 (M+H)+, 829.2 (2M+H)+.

Step 7 (1-{2-[7-(3-Fluoro-benzenesulfonyl)-chroman-4-yl]-ethyl}-pyrrolidin-3-yl) methyl-carbamic acid tert-butyl ester

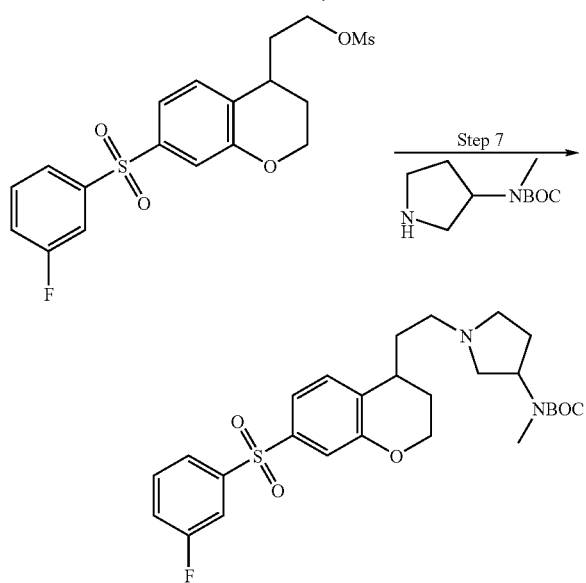

2-[7-(3-fluoro-benzenesulfonyl)-chroman-4-yl]-ethyl ester (0.1 g, 0.24 mmol) and 3-(N-tert-butoxycarbonyl-N-methyl amino)-pyrrolidine (1.0 ml, 4.3 mmol) were dissolved in THF (2.0 ml). The mixture was set up in a microwave reactor at 120° C. for 3 hours. The reaction mixture was partitioned between water and EtOAc. The EtOAc layer was dried with MgSO₄, filtered and concentrated. The residue was purified with preparative-TLC to give (1-{2-[7-(3-Fluoro-benzenesulfonyl)-chroman-4-yl]-ethyl}-pyrrolidin-3-yl)-methyl-carbamic acid tert-butyl ester (0.9 g), MS: 519.4(M+H)+.

Step 8 (1-{2-[7-(3-Fluoro-benzenesulfonyl)-chroman-4-yl]-ethyl}-pyrrolidin-3-yl)-methylamine

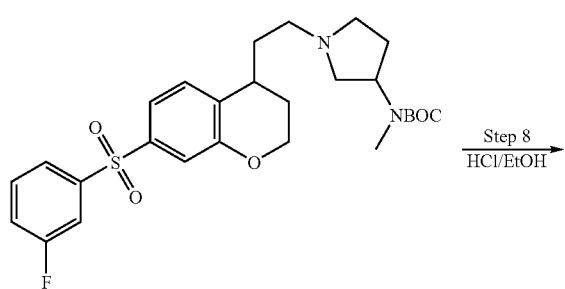

(1-{2-[7-(3-Fluoro-benzenesulfonyl)-chroman-4-yl]-ethyl}-pyrrolidin-3-yl)-methyl-carbamic acid tert-butyl ester (0.9 g) was dissolved in 2N HCl in EtOH (2 ml) and the mixture was heated at 60° C. for 40 minutes. The reaction mixture was cooled to room temperature and was quenched with saturated NaHCO₃, extracted with methylene chloride, dried with MgSO₄, filtered, concentrated and purified with preparative TLC (10% MeOH in methylene chloride with 1% Et3N) to give (1-{2-[7-(3-fluoro-benzenesulfonyl)-chroman-4-yl]-ethyl}-pyrrolidin-3-yl)-methyl-amine, which was treated with a few drops of 2N HCl in EtOH and dried under vacuum to give (1-{2-[7-(3-Fluoro-benzenesulfonyl)-chroman-4-yl]-ethyl}-pyrrolidin-3-yl)-methyl-amine HCl salt: 61.8 mg, MS: 419.5 (M+H)+.

Similarly prepared from the mesylate of step 6, were:
(1-{2-[7-(3-Fluoro-benzenesulfonyl)-chroman-4-yl]-ethyl}-pyrrolidin-3-yl)-dimethyl-amine, 60% yield, MS: 433.3 (M+H)⁺; and {2-[7-(3-Fluoro-benzenesulfonyl)-chroman-4-yl]-ethyl}-pyrrolidin-3-yl-amine, 61% yield, MS: 405.5(M+H)⁺.

Example 8

[7-(3-Fluoro-benzenesulfonyl)-chroman-4-ylm-ethyl]-methyl-amine

The synthetic procedure described in this Example was carried out according to the process shown in Scheme J.

SCHEME J

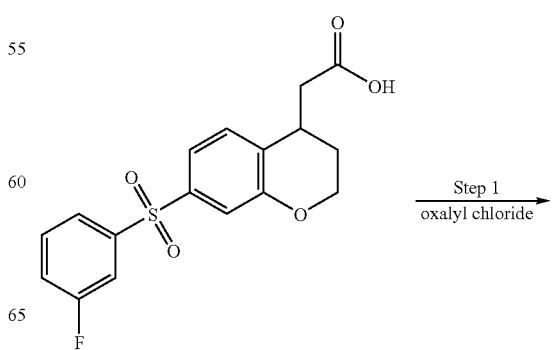

To a solution of [7-(3-Fluoro-benzenesulfonyl)-chroman-4-yl]-acetic acid (1.0 g, 2.85 mmol) in CH$_2$Cl$_2$ (20 ml) at 0° C. was added oxalyl chloride (2.85 ml, 2M in CH$_2$Cl$_2$, 5.71 mmol) followed by 3 drops of DMF. The reaction mixture was stirred in the ice bath for 3 hours. The solvent was removed, and toluene (10 ml) was added to the residue, and was evaporated via vacuum to remove any remaining oxalyl chloride. The crude 7-(3-fluoro-benzenesulfonyl)-chroman-4-yl]-acetyl chloride was obtained as a syrup.

Step 2 7-(3-Fluoro-benzenesulfonyl)-4-isocyanatomethyl-chroman

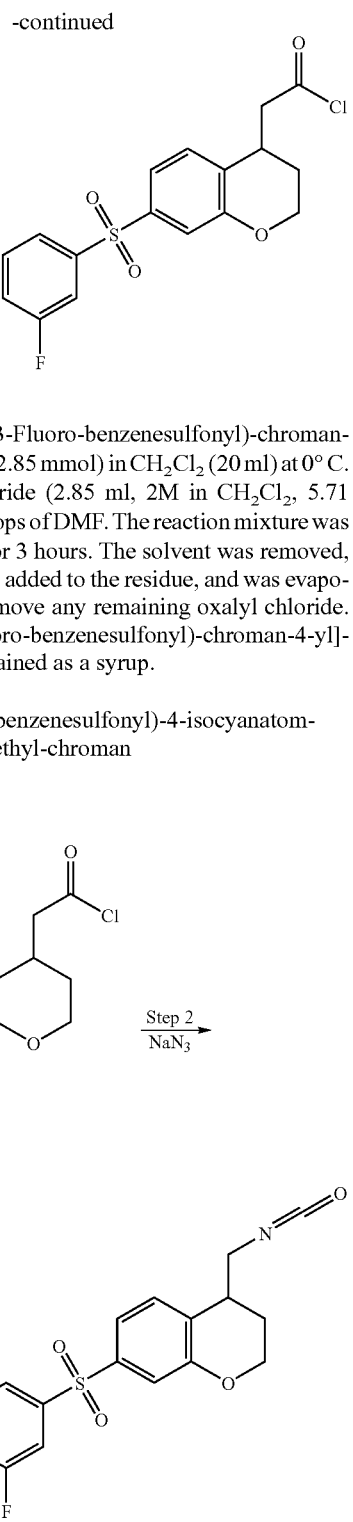

A solution of NaN$_3$ (0.56 g, 8.61 mmol) in H$_2$O (2 ml) was added to a solution of 7-(3-fluoro-benzenesulfonyl)-chroman-4-yl]-acetyl chloride in acetone (10 ml) at 0° C. The mixture was stirred in the ice bath for 30 minutes then at room temperature overnight. The mixture was partitioned between water and EtOAc. The EtOAc layer was dried with MgSO$_4$, filtered, concentrated and purified with flash chromatography

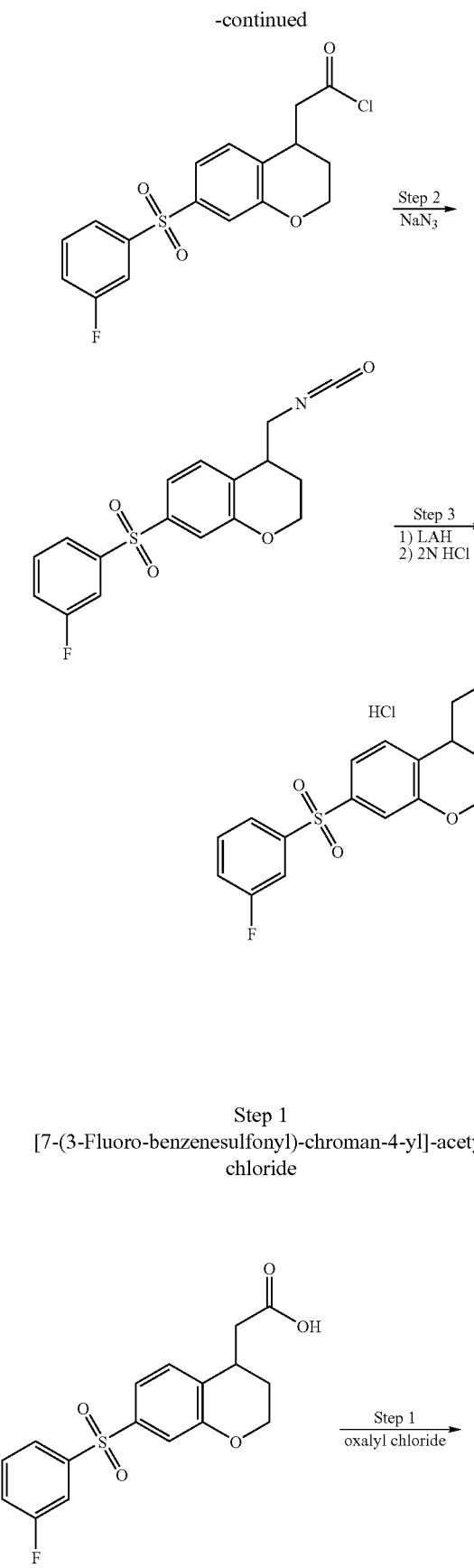

Step 1
[7-(3-Fluoro-benzenesulfonyl)-chroman-4-yl]-acetyl chloride to give 7-(3-fluoro-benzenesulfonyl)-4-isocyanatomethyl-chroman as a clear waxy oil: 0.55 g, MS: 348.1(M+H)$^+$, 389.2(M+CH$_3$CN+H)$^+$.

Step 3 [7-(3-Fluoro-benzenesulfonyl)-chroman-4-ylmethyl]-methyl-amine

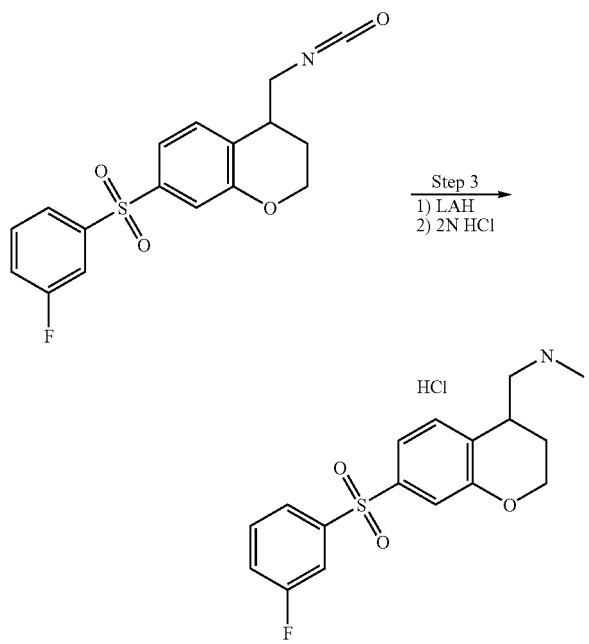

To a solution of 7-(3-fluoro-benzenesulfonyl)-4-isocyanatomethyl-chroman (0.12 g, 0.35 mmol) in THF (15 ml) at 0° C. was added LiAlH$_4$ (0.52 ml, 1.0 M in THF, 0.525 mmol). The mixture was stirred at 0° C. for 2 hours, then was quenched with one drop of H$_2$O, 3 drops of 2N NaOH, and 3 drops of H$_2$O again. The precipitate was filtered off. The solution was diluted with EtOAc, washed with water, dried with MgSO$_4$, filtered and concentrated. The residue was purified with preparative TLC to give [7-(3-Fluoro-benzenesulfonyl)-chroman-4-ylmethyl]-methyl-amine free base, which was further treated with a few drops of 2N HCl in EtOH and dried under vacuum to give the corresponding HCl salt: 33.5 mg. MS: 336.2 (M+H)$^+$, 377.2 (M+CH$_3$CN+H)$^+$, 671.3 (2M+H)$^+$.

Example 9

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 10

Radioligand Binding Studies

This example illustrates in vitro radioligand binding studies of compound of formula I.

The binding activity of compounds of this invention in vitro was determined as follows. Duplicate determinations of 5-$HT_6$ ligand affinity were made by competing for binding of [$^3$H]LSD in cell membranes derived from HEK293 cells stably expressing recombinant human 5-$HT_6$ receptor. Duplicate determinations of 5-$HT_{2A}$ ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO-K1 cells stably expressing recombinant human 5-$HT_{2A}$ receptor. Membranes were prepared from HEK 293 cell lines by the method described by Monsma et al., Molecular Pharmacology, Vol. 43 pp. 320-327 (1993), and from CHO-K1 cell lines as described by Bonhaus et al., Br J Pharmacol. June; 115(4): 622-8 (1995).

For estimation of affinity at the 5-$HT_6$ receptor, all determinations were made in assay buffer containing 50 mM Tris-HCl, 10 mM $MgSO_4$, 0.5 mM EDTA, 1 mM ascorbic acid, pH 7.4 at 37° C., in a 250 microliter reaction volume. For estimation of affinity at the 5-$HT_{2A}$ receptor all determinations were made in assay buffer containing 50 mM Tris-HCl, 5 mM ascorbic acid, 4 mM CaCl2, pH 7.4 at 32° C., in a 250 microliter reaction volume.

Assay tubes containing [$^3$H] LSD or [$^3$H]Ketanserin (5 nM), competing ligand, and membrane were incubated in a shaking water bath for 75 min. at 37° C. (for 5-$HT_6$) or 60 min. at 32° C. (for 5-$HT_{2A}$), filtered onto Packard GF-B plates (pre-soaked with 0.3% PEI) using a Packard 96 well cell harvester and washed 3 times in ice cold 50 mM Tris-HCl. Bound [$^3$H] LSD or [$^3$H]Ketanserin were determined as radioactive counts per minute using Packard TopCount.

Displacement of [$^3$H]LSD or [$^3$H]Ketanserin from the binding sites was quantified by fitting concentration-binding data to a 4-parameter logistic equation:

$$\text{binding} = \text{basal} + \left( \frac{Bmax\text{-basal}}{1 + 10^{-Hill(\log[ligand] - \log IC_{50})}} \right)$$

where Hill is the Hill slope, [ligand] is the concentration of competing radioligand and $IC_{50}$ is the concentration of radioligand producing half-maximal specific binding of radioligand. The specific binding window is the difference between the Bmax and the basal parameters. Using the procedures of this Example, compounds of Formula I were tested and found to be selective 5-$HT_6$ antagonists, selective 5-$HT_{2A}$ antagonists, or both. For example, the compound C-(7-benzenesulfonyl-chroman-4-yl)-methylamine. exhibited a pKi of approximately 9.14 for 5-$HT_6$, and a pKi of approximately 7.69 for 5-$HT_{2A}$.

Example 11

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before Ti. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. Behav. Brain Res. 31, 47-59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of formula I:

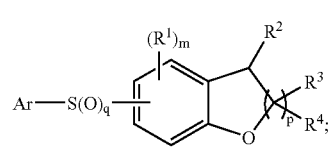

or a pharmaceutically acceptable salt thereof, wherein:
m is from 0 to 3;
p is 2;
q is 0, 1 Or 2;
Ar is optionally substituted aryl or optionally substituted heteroaryl;
each $R^1$ is independently halo, alkyl, haloalkyl, heteroalkyl, cyano, —S(O)$_t$—R$^a$, —C(=O)—NR$^b$R$^c$, —SO$_2$—NR$^b$R$^c$, —N(R$^d$)—C(=O)—R$^e$, —C(=O)N(R$^d$)—, or —C(=O)—R$^e$, where t is from 0 to 2, and R$^a$, R$^b$, R$^c$, R$^d$ and R$^e$ each independently is hydrogen or alkyl, and;
$R^2$ is

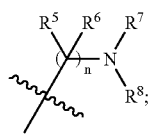

n is from 1 to 3;
$R^3$ and $R^4$ each independently is hydrogen or alkyl;
$R^5$ and $R^6$ each independently is hydrogen or alkyl, or $R^5$ and $R^6$ together may form =NR$^f$ wherein R$^f$ is hydrogen or alkyl; and
$R^7$ and $R^8$ each independently is hydrogen or alkyl, or one of $R^7$ and $R^8$ is hydrogen and the other is an optionally substituted 5- or six membered heteroaryl or heterocyclyl containing one or two nitrogens, or $R^7$ and $R^8$ together with the nitrogen to which they are attached may form an amidinyl group, a urea group, a guanidinyl group, or a five- or six-membered heterocyclic ring that optionally includes an additional heteroatom selected from O, N and S and which is optionally substituted with amino, or one of $R^7$ and $R^8$ and one of $R^5$ and $R^6$ together with the atoms to which they are attached may form a five- or six-membered heterocyclic ring that optionally includes an additional heteroatom selected from O, N and S.

2. The compound of claim 1 wherein q is 2.

3. The compound of claim 2, wherein m is 0 or 1.

4. The compound of claim 3, wherein Ar is optionally substituted phenyl.

5. The compound of claim 4, wherein n is 1.

6. The compound of claim 5, wherein $R^5$ and $R^6$ are hydrogen.

7. The compound of claim 6, wherein $R^7$ and $R^8$ are hydrogen.

8. The compound of claim 6, wherein one of $R^7$ and $R^8$ is hydrogen and the other is alkyl.

9. The compound of claim 6, wherein one of $R^7$ and $R^8$ is hydrogen and the other is pyrrolidinyl.

10. The compound of claim 6, wherein $R^7$ and $R^8$ together with the nitrogen to which they are attached form an amidinyl group.

11. The compound of claim 6, wherein $R^7$ and $R^8$ together with the nitrogen to which they are attached form guanidinyl group.

12. The compound of claim 6, wherein $R^7$ and $R^8$ together with the nitrogen to which they are attached form a urea group.

13. The compound of claim 4, wherein n is 2.

14. The compound of claim 13, wherein $R^5$ and $R^6$ are hydrogen.

15. The compound of claim 14, wherein $R^7$ and $R^8$ are hydrogen.

16. The compound of claim 14, wherein one of $R^7$ and $R^8$ is hydrogen and the other is alkyl.

17. The compound of claim 14, wherein one of $R^7$ and $R^8$ is hydrogen and the other is optionally substituted pyrrolidinyl.

18. The compound of claim 14, wherein $R^7$ and $R^8$ together with the nitrogen to which they are attached form an amidinyl group.

19. The compound of claim 14, wherein $R^7$ and $R^8$ together with the nitrogen to which they are attached form a guanidinyl group.

20. The compound of claim 1, wherein said compound is of formula III:

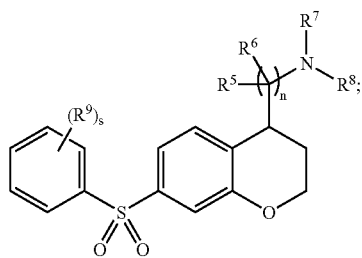

wherein:
s is from 0 to 4;
each $R^9$ is independently halo, alkyl, alkoxy, haloalkyl, heteroalkyl, cyano, —S(O)$_r$—R$^a$, —C(=O)—NR$^b$R$^c$, —SO$_2$—NR$^b$R$^c$, —N(R$^d$)—C(=O)—R$^e$, or —C(=O)—R$^e$, where r is from 0 to 2, and R$^a$, R$^b$, R$^c$, R$^d$ and R$^e$ each independently is hydrogen or alkyl; and
n, $R^5$, $R^6$, $R^7$ and $R^8$ are as recited in claim 1.

21. The compound of claim 1, wherein said compound is of formula IV:

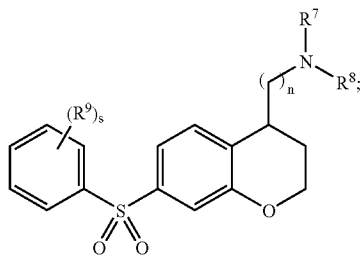

wherein:
n is 1 or 2;
s is 0 or 1;
$R^9$ is halo, alkyl, alkoxy, or haloalkyl; and
$R^7$ and $R^8$ are as recited in claim 1.

22. A composition comprising an effective amount of the compound of claim 1 in admixture with a pharmaceutically acceptable carrier.

23. The compound of claim 1, wherein said compound is selected from the group consisting of:
2-(7-Benzenesulfonyl-chroman-4-yl)-ethylamine;
C-(7-Benzenesulfonyl-chroman-4-yl)-methylamine;
(7-Benzenesulfonyl-chroman-4-ylmethyl)-methyl-amine;
N-(7-Benzenesulfonyl-chroman-4-ylmethyl)-guanidine;

(7-Benzenesulfonyl-chroman-4-ylmethyl)-urea;
N-(7-Benzenesulfonyl-chroman-4-ylmethyl)-acetamidine;
(1-{2-[7-(3-Fluoro-benzenesulfonyl)-chroman-4-yl]-ethyl}-pyrrolidin-3-yl)-methyl-amine;
(1-{2-[7-(3-Fluoro-benzenesulfonyl)-chroman-4-yl]-ethyl}-pyrrolidin-3-yl)-dimethyl-amine;
{2-[7-(3-Fluoro-benzenesulfonyl)-chroman-4-yl]-ethyl}-pyrrolidin-3-yl-amine; and
[7-(3-Fluoro-benzenesulfonyl)-chroman-4-ylmethyl]-methyl-amine.

* * * * *